US012778898B2

(12) United States Patent
Loeb et al.

(10) Patent No.: US 12,778,898 B2
(45) Date of Patent: Nov. 3, 2026

(54) THREE-DIMENSIONAL PRINTED STRUCTURAL SILOXANES HAVING CONTROLLED DRUG RELEASE

(71) Applicant: Lawrence Livermore National Security, LLC, Livermore, CA (US)

(72) Inventors: Colin Loeb, Fairfield, CA (US); Eric B. Duoss, Dublin, CA (US); Jeremy Lenhardt, Tracy, CA (US); Du Nguyen, Fremont, CA (US); Thomas S. Wilson, San Leandro, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1413 days.

(21) Appl. No.: 16/374,629

(22) Filed: Apr. 3, 2019

(65) Prior Publication Data

US 2020/0315975 A1 Oct. 8, 2020

(51) Int. Cl.

| | |
|---|---|
| ***A61K 9/50*** | (2006.01) |
| ***A61K 9/48*** | (2006.01) |
| ***B29C 64/118*** | (2017.01) |
| ***B33Y 10/00*** | (2015.01) |
| ***B33Y 70/10*** | (2020.01) |
| ***B33Y 80/00*** | (2015.01) |
| ***C08L 83/04*** | (2006.01) |
| ***C09D 11/03*** | (2014.01) |
| ***C09D 11/102*** | (2014.01) |
| *B29K 83/00* | (2006.01) |
| *B29K 105/00* | (2006.01) |
| *C08G 77/00* | (2006.01) |
| *C08K 3/36* | (2006.01) |

(52) U.S. Cl.

CPC .......... *A61K 9/5031* (2013.01); *A61K 9/4858* (2013.01); *A61K 9/501* (2013.01); *A61K 9/5089* (2013.01); *B29C 64/118* (2017.08); *B33Y 10/00* (2014.12); *B33Y 70/10* (2020.01); *B33Y 80/00* (2014.12); *C08L 83/04* (2013.01); *C09D 11/03* (2013.01); *C09D 11/102* (2013.01); *B29K 2083/00* (2013.01); *B29K 2105/0076* (2013.01); *C08G 77/70* (2013.01); *C08G 77/80* (2013.01); *C08K 3/36* (2013.01); *C08L 2201/06* (2013.01); *C08L 2203/02* (2013.01); *C08L 2207/53* (2013.01)

(58) Field of Classification Search

None

See application file for complete search history.

(56) References Cited

U.S. PATENT DOCUMENTS 6,416,740 B1 * 7/2002 Unger .................. A61K 49/223 424/9.5
8,333,946 B2 12/2012 Gottschalk-Gaudig et al.
2004/0005360 A1 * 1/2004 Wang .................... B33Y 80/00 424/473
2007/0287771 A1 12/2007 Yamazaki et al.
2010/0239871 A1 9/2010 Scheffer et al.
2014/0356590 A1 12/2014 Hoffee et al.
2016/0198576 A1 7/2016 Lewis et al.
2016/0214075 A1 * 7/2016 Suslick .................... B01J 13/14
2017/0039898 A1 2/2017 Kim
2017/0225491 A1 8/2017 Miller
2017/0273900 A1 9/2017 Arps et al.
2018/0066115 A1 3/2018 Achenbach et al.

FOREIGN PATENT DOCUMENTS

CN 104623737 * 5/2015
EP 1433749 A1 6/2004
WO 2017081028 A1 5/2017

OTHER PUBLICATIONS

Durban et al. (Macromol. Rapid Commun., 39, 1700563. pp. 1-6) Custom SD Printable Silicones with Tunable Stiffness (Year: 2018).*

Riess (Tetrahedron, 58, 4113-4131) Fluorous micro-nanophases with a biomedical perspective (Year: 2002).*

Durban et al., U.S. Appl. No. 15/721,528, filed Sep. 29, 2017.

International Search Report and Written Opinion from PCT Application No. PCT/US18/53452, dated Oct. 26, 2018.

SIMTEC, "Reinforcing Fillers in Liquid Silicone Rubber Compounds," SIMTEC, Dec. 11, 2017, 5 pages, retrieved from https://www.simtec-silicone.com/reinforcing-fillers-liquid-silicone-rubber-compounds/.

Duoss et al., "Three-Dimensional Printing of Elastomeric, Cellular Architectures with Negative Stiffness," Advanced Functional Materials, vol. 24, 2014, pp. 4905-4913.

Schmalzer et al., "Gamma radiation effects on siloxane-based additive manufactured structure," Radiation Physics and Chemistry, vol. 130, 2017, pp. 103-111.

Aerosil, "Aerosil R 9200," Aerosil, Technical Data Sheet, Jan. 2018, 1 page.

Grassie et al., "The Thermal Degradation of Polysiloxanes—Part 4: Poly(dimethyl/diphenyl siloxane)," Polymer Degradation and Stability, vol. 2, 1980, pp. 67-83.

Teixeira et al., "Microencapsulation of Active Ingredients Using PDMS as Shell Material, " Macromolecules, vol. 47, Nov. 21, 2014, pp. 8231-8237.

Vilanova et al., "Preparation of Novel Silicone Multicompartment Particles by Multiple Emulsion Templating and Their use as Encapsulating Systems," Langmuir, vol. 29, Nov. 21, 2013, pp. 15414-15422.

Zoldesi et al., "Deformable Hollow Hybrid Silica/Siloxane Colloids by Emulsion Templating," Langmuir, vol. 22, No. 9, Mar. 30, 2006, pp. 4343-4352.

(Continued)

*Primary Examiner* — Tigabu Kassa

(74) *Attorney, Agent, or Firm* — Zilka-Kotab, P.C.

(57) ABSTRACT

According to one embodiment, a core-shell microsphere includes a polyorganosiloxane shell, and a core inside the shell, the core having a carrier and at least one component, where the at least one component is configured to be released post processing. In addition, an average diameter of the polyorganosiloxane shell is in a range of greater than about 1 micron to less than about 100 microns.

31 Claims, 14 Drawing Sheets

(56) References Cited

OTHER PUBLICATIONS

Zoldesi et al., “Synthesis of Monodisperse Colloidal Spheres, Capsules, and Microballoons,” Advanced Materials, vol. 17, No. 7, Apr. 2005, pp. 924-928.

* cited by examiner

FIG. 8A
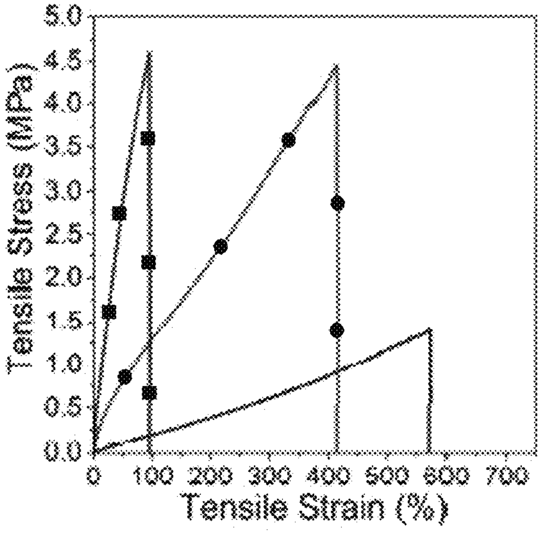
FIG. 8B
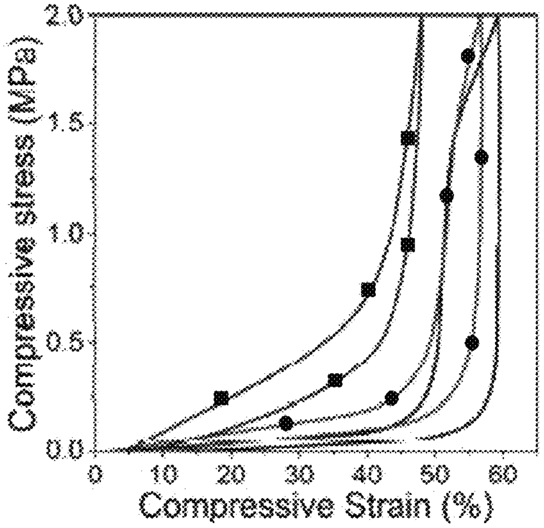
FIG. 8C
FIG. 8D
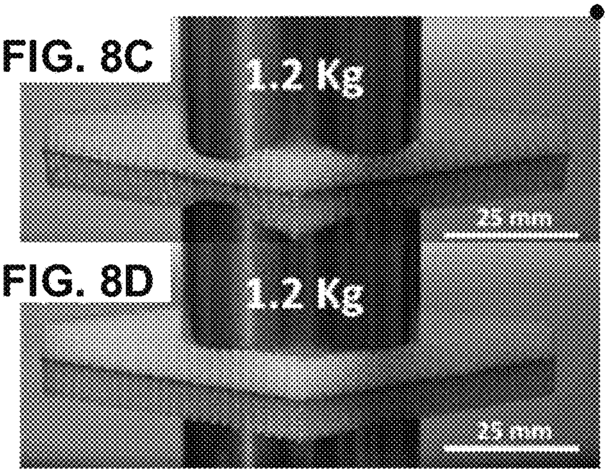
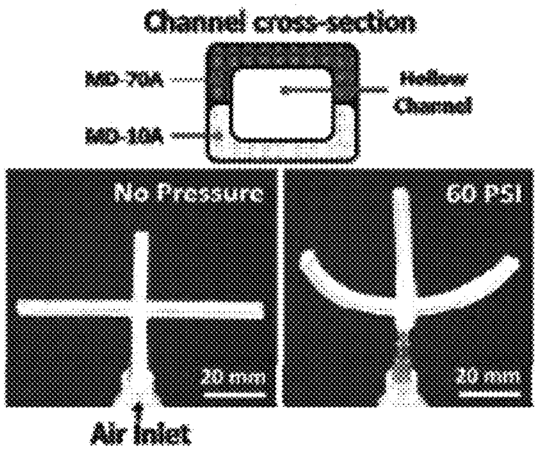
FIG. 8E FIG. 13A
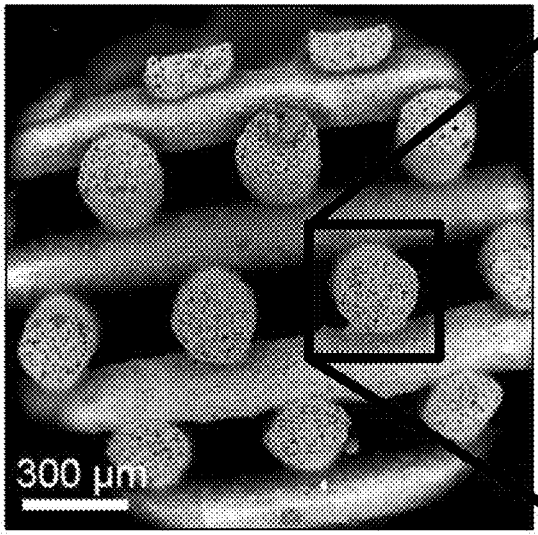
FIG. 13B
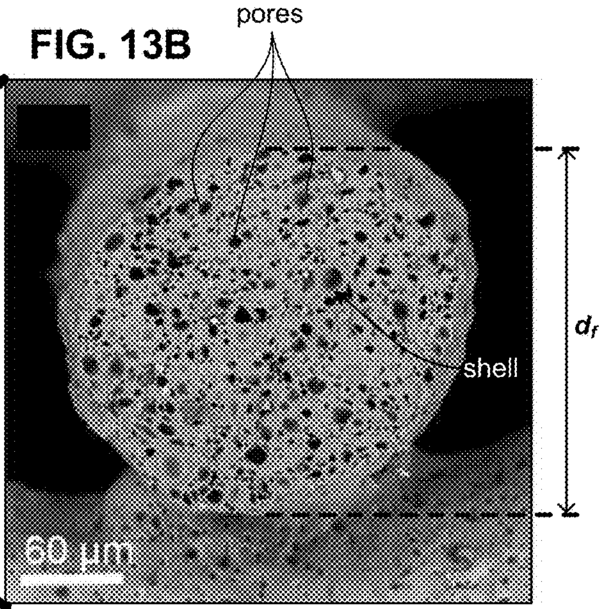
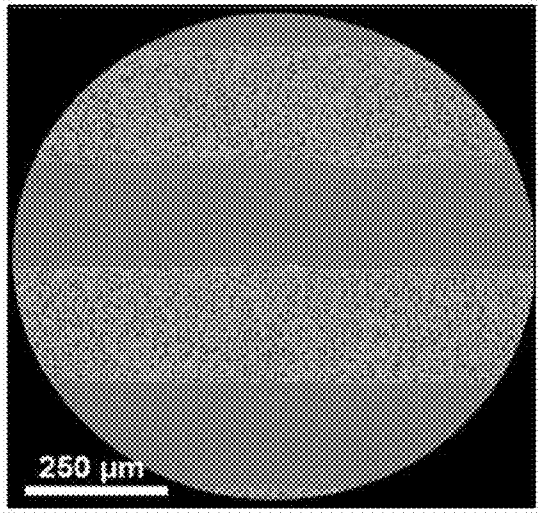
FIG. 13C
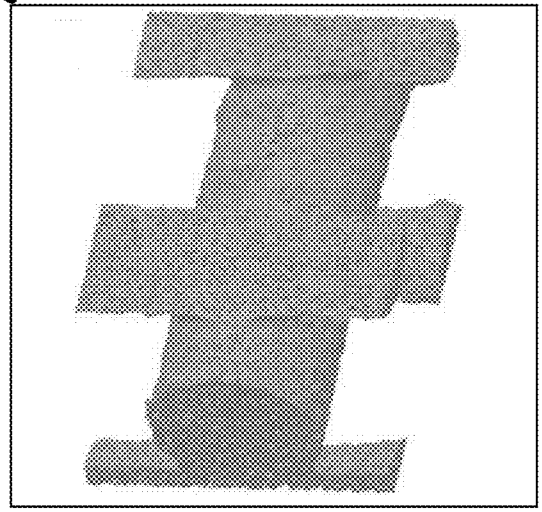
FIG. 13D

THREE-DIMENSIONAL PRINTED STRUCTURAL SILOXANES HAVING CONTROLLED DRUG RELEASE

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to additive manufacturing of silicone materials, and more particularly, this invention relates to silicone-based inks having core-shell microspheres for additive manufacturing and additive manufacturing processes using such inks.

BACKGROUND

The field of three-dimensional (3D) printed silicone materials is new and largely unexplored. The flowable nature of liquid silicone materials suggests that silicone material may be used in a direct ink write (DIW) process of additive manufacturing (AM); however, the formation of 3D structures that retain their shape has remained elusive. On the other hand, solid silicone material cannot be used as ink in additive manufacturing because it in unflowable and cannot be extruded from the nozzle during printing.

Conventional 3D printed silicones through the DIW process produce intricate structures through rheological modification by the rendering of a nano-scale network between silica filler and rheological additive, thus allowing shape retention of the printed structure. However, the filaments that build the printed structures through DIW tend to be largely homogenous and devoid of internal microstructure or functionality.

It would be desirable to impart functionality to the microstructure formed with silicone inks.

SUMMARY

In one embodiment, a core-shell microsphere includes a polyorganosiloxane shell, and a core inside the shell, the core having a carrier and at least one component, where the at least one component is configured to be released post processing. In addition, an average diameter of the polyorganosiloxane shell is in a range of greater than about 1 micron to less than about 100 microns.

In another embodiment, a silicone-based ink for additive manufacturing includes a vinyl-terminated diphenyl siloxane macromer, a treated silica hydrophobic reinforcing filler, a rheology modifying additive, and a plurality of core-shell microspheres.

In yet another embodiment, a product of additive manufacturing with a silicone-based ink having core-shell microspheres includes a vinyl-terminated siloxane macromer, a hydrophobic reinforcing filler, a rheology modifying additive, and a plurality of core-shell microspheres. The product has a plurality of continuous filaments.

Other aspects and advantages of the present invention will become apparent from the following detailed description, which, when taken in conjunction with the drawings, illustrate by way of example the principles of the invention.

BRIEF DESCRIPTION OF THE DRAWINGS

FIG. 8A is a plot of tensile stress versus tensile strain, according to various embodiments.

FIG. 8B is a plot of compressive performance, according to various embodiments.

FIGS. 8C and 8D are images of a physical demonstration of stiffness of 3D printed silicone-based lattices, according to various embodiments.

FIG. 8E is a diagram of a 3D-printed air-driven soft robotic actuator, according to one embodiment.

FIG. 13A is a scanning electron micrograph of a cross-section of a 3D printed part using silicone ink having core-shell microspheres, according to one embodiment.

FIG. 13B is a magnified view of a portion of the image of FIG. 13A.

FIG. 13C is an image slice of a 3D printed part using silicone ink having core-shell microspheres from micro CT analysis, according to one embodiment.

FIG. 13D is a rendering from micro CT analysis of a 3D printed part using silicone ink having core-shell microspheres, according to one embodiment.

DETAILED DESCRIPTION

Figure 1:
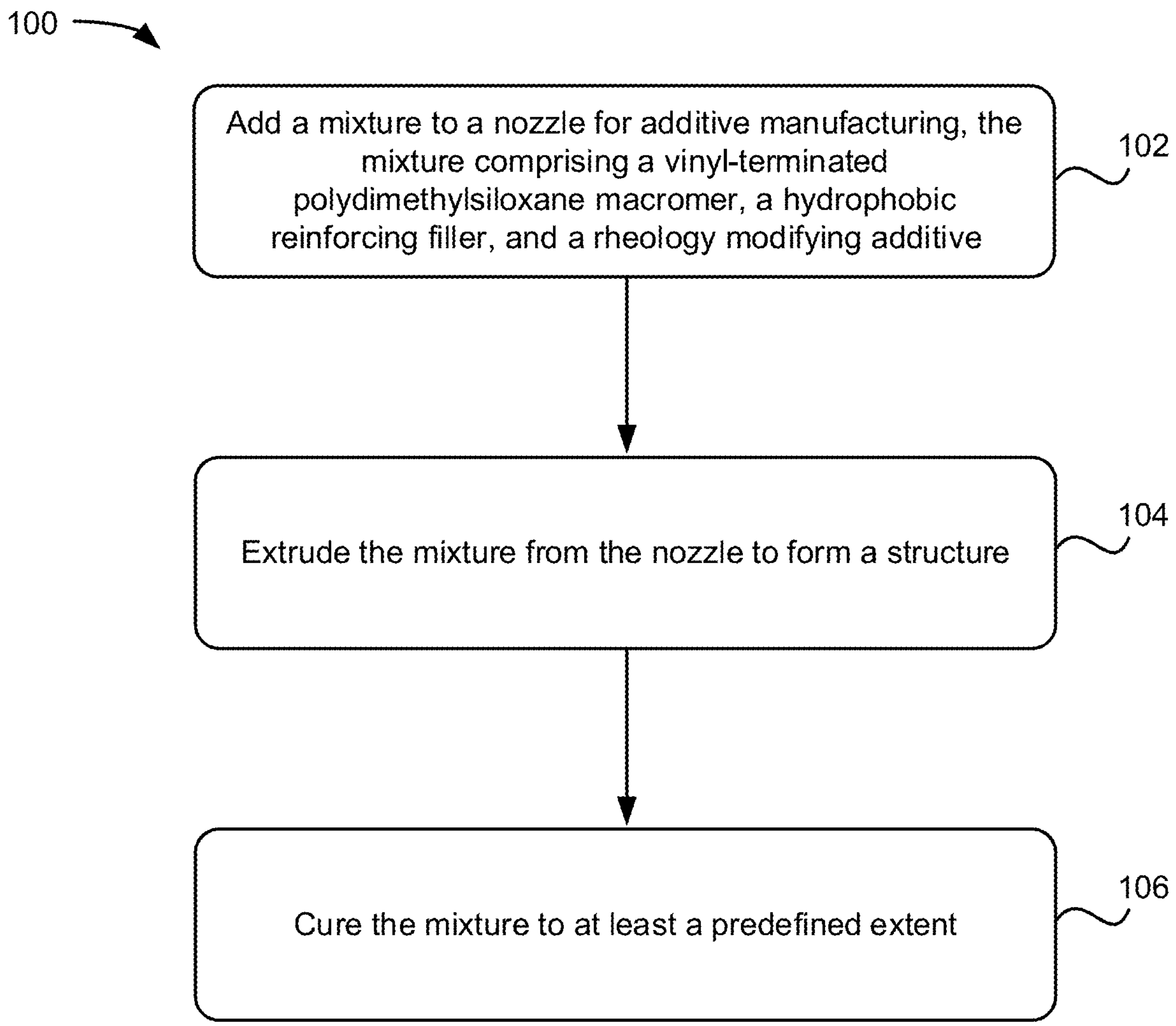
FIG. 1 is a flow chart of a method, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As also used herein, the term "about" denotes an interval of accuracy that, ensures the technical effect of the feature in question. In various approaches, the term "about" when combined with a value, refers to plus and minus 10% of the reference value. For example, a thickness of about 10 nm refers to a thickness of 10 nm±1 nm, a temperature of about 50° C. refers to a temperature of 50° C.±5° C., etc.

It is also noted that, as used in the specification and the appended claims, wt % is defined as the percentage of weight of a particular component is to the total weight/mass of the mixture. Vol % is defined as the percentage of volume of a particular compound to the total volume of the mixture or compound. Mol % is defined as the percentage of moles of a particular component to the total moles of the mixture or compound. Atomic % (at %) is defined as a percentage of one type of atom relative to the total number of atoms of a compound.

Ambient room temperature may be defined as a temperature in a range of about 20° C. to about 25° C.

The present disclosure includes several descriptions of exemplary "inks" used in an additive manufacturing process to form the inventive optics described herein. It should be understood that "inks" (and singular forms thereof) may be used interchangeably and refer to a composition of matter comprising a plurality of particles coated with/dispersed throughout a liquid phase such that the composition of matter may be "written," extruded, printed, or otherwise deposited to form a layer that substantially retains its as-deposited geometry and shape without excessive sagging, slumping, or other deformation, even when deposited onto other layers of ink, and/or when other layers of ink are deposited onto the layer. As such, skilled artisans will understand the presently described inks to exhibit appropriate rheological properties to allow the formation of monolithic structures via deposition of multiple layers of the ink (or in some cases multiple inks with different compositions) in sequence.

The following description discloses several preferred structures formed via direct ink writing (DIW), extrusion freeform fabrication, or other equivalent techniques and therefore exhibit unique structural and compositional characteristics conveyed via the precise control allowed by such techniques.

The following description discloses several preferred embodiments of silicone-based formulations and/or related systems and methods.

In one general embodiment, a core-shell microsphere includes a polyorganosiloxane shell, and a core inside the shell, the core having a carrier and at least one component, where the at least one component is configured to be released post processing. In addition, an average diameter of the polyorganosiloxane shell is in a range of greater than about 1 micron to less than about 100 microns.

In another general embodiment, a silicone-based ink for additive manufacturing includes a vinyl-terminated diphenyl siloxane macromer, a treated silica hydrophobic reinforcing filler, a rheology modifying additive, and a plurality of core-shell microspheres.

In yet another general embodiment, a product of additive manufacturing with a silicone-based ink having core-shell microspheres includes a vinyl-terminated siloxane macromer, a hydrophobic reinforcing filler, a rheology modifying additive, and a plurality of core-shell microspheres. The product has a plurality of continuous filaments.

A list of acronyms used in the description is provided below.

3D Three-dimensional
AM Additive manufacturing
C Celsius
cSt centiStokes
DIW Direct Ink Writing
DPS diphenylsiloxane
ETCH 1-ethynyl-1-cyclohexanol
FCT face centered tetragonal
g gram
HMDZ hexamethyldisilazane
kg kilogram
MQ Mono and tetra siloxane copolymer
mL milliliters
Pa Pascals
PDMS polydimethylsiloxane
PFC Perfluorocarbon
PHMS poly(hydrogenmethylsiloxane)
ppm parts per million
Pt Platinum
rpm revolutions per minute
SEM Scanning electron microscopy
THF Tetrahydrofuran
W Watt
Wt. % weight percent
vol % volume percent Inks with a specific rheology used in 3D printing allow the resulting 3D printed structures to retain their shape for an extended period of time before curing.

According to various embodiments, silicone-based inks with appropriate rheological behavior for 3D printing result in printing 3D porous structures with controlled architectures. Various embodiments described herein demonstrate the capability to tune the stiffness of printable silicone materials by controlling the chemistry, network formation, and crosslink density of silicone-based ink formulations in order to overcome the challenging interplay between ink development, post-processing, material properties, and performance. Various embodiments described herein identify materials and methods by which to prepare custom-tailored 3D printable silicone materials through DIW processes.

Moreover, various embodiments described herein demonstrate that through adjustments to the chain lengths of functional silicone-based materials and through the incorporation of reinforcing filler materials, silicones can be prepared with tunable stiffness, unlocking the ability to print functional parts exhibiting anisotropic behavior and properties when printed in tandem or dynamically mixed. Furthermore, custom formulations prepared according to the teaching herein unlock the ability to control the chemistry of silicone-based materials, affecting their aging behavior, material compatibility and biocompatibility, and surface chemistry to impart adhesiveness. Described herein are a series of low temperature stable 3D printable silicones with tunable stiffness developed through a study of silicone rheology, pseudoplasticity, filler loading, and cure inhibition, to facilitate the printing of silicone materials with an extended working lifetime.

Various embodiments described herein, materials and methods may be used to prepare 3D printable silicone materials through DIW processes that contain a custom-tailored intra-filament micro-structure. In some approaches, the intra-filament structure may be utilized to introduce functionally and specialized properties to the printed structure.

Silicone elastomers have broad versatility within a variety of advanced material applications, such as soft robotics, biomedical devices, and metamaterials. However, non-polar silicone materials are not naturally pseudoplastic or thixotropic in which a solid silicone material becomes liquid with applied stress. In would be desirable to develop an ink using non-polar silicone materials so that silicone-based 3D structure may be formed.

In one embodiment, a silicone-based ink for additive manufacturing includes a vinyl-terminated siloxane macromer, a hydrophobic reinforcing filler, and a rheology modifying additive. In some approaches, the vinyl-terminated siloxane macromer may be an oligomeric organosiloxane macromer. In other approaches, the vinyl-terminated siloxane macromer may be a polymeric organosiloxane macromer. In an exemplary approach, the vinyl-terminated siloxane macromer may be a vinyl-terminated polydimethylsiloxane (PDMS) macromer. In some approaches, the vinyl-terminated siloxane macromer may have a viscosity in a range of about 500 centiStoke and about 50,000 centiStoke (cSt).

In one embodiment, a silicone-based ink for additive manufacturing includes a vinyl-terminated polydimethylsiloxane-diphenyl siloxane (DPS) macromer, hydrophobic reinforcing filler, and a rheology modifying additive. In some approaches, a vinyl-terminated PDMS-DPS macromer may have a viscosity in a range of about 500 cSt to about 50,000 cSt.

In some embodiments of the silicone-based ink, the hydrophobic reinforcing filler may be treated silica. In some approaches, the treated silica may have a surface area in a range of about 50 $m^2/g$ to about 250 $m^2/g$. In a preferred approach, the treated silica may have a surface area in a range of about 100 $m^2/g$ to 200 $m^2/g$ for imparting reinforcement while alleviating an increase in viscosity that could obstruct the extrusion process. In some approaches, the treated silica may be hexamethyldisilazane (HMDZ)-treated silica. In other approaches, additional treated silicas with increased hydrophobicity may also be used. In some approaches, a silicone-based ink may include a composite of PDMS-DPS and hydrophobic filler such as HMDZ-treated silica. The hydrophobic reinforcing filler, such as HMDZ-treated silica, may be included to ensure a long-term stability of 3D printed silicone components prior to curing. HMDZ treatment of silica may involve capping the silanol groups of the silica with HMDZ to yield trimethylsilanes and a hydrophobic filler surface.

In some embodiments, fumed silica in the silicone-based ink may be in a range of about 5 wt. % to about 50 wt. % of total composition of the ink, and preferably in a range of about 12 wt % to about 35 wt. % of total composition of the ink. In some approaches, silica fillers with reduced surface area allow an increase degree of silica loading without over-saturating the liquid ink matrix, and thereby resulting in highly stiff printable silicone materials. In some approaches, the effective concentration of fumed silica may be determined from the surface area of the fumed silica using known techniques.

In other approaches, an untreated silanol-containing filler may likely result in crepe hardening (i.e. thickening of uncured silicones) of the silicone under prolonged storage before curing. Moreover, premature hardening of the silicone may yield a progressive increase in material stiffness due in part to condensation reactions between neighboring silanol groups. Furthermore, the use of untreated silica fillers may reduce the mechanical strength and alter the physical properties of silicones. In some cases, untreated silica fillers may retain more moisture than hydrophobic fillers, and thus may be undesirable for long term applications.

In various embodiments, silicone-based inks may be prepared with a proper rheology for 3D printing in which structures with pre-defined dimensions are formed.

In some embodiments, a rheology modifying additive may be added to impart silicone pseudoplasticity. Rheology modifying additives impart thixotropy in silicone materials. A rheology modifying additive may be a thixotropic additive that imparts pseudoplasticity in silicone elastomers. In some approaches, the rheology modifying additive may be a silicone polyether, a methylvinyl siloxane (or dimethyl siloxane), dimethoxy (glycidoxypropyl)-terminated, glycerol, 2-propanol or combinations thereof. In some embodiments, the silicone-based ink may include a rheology modifying additive in a range of about 0.01 wt. % to about 10.0 wt % of total composition, and preferably about 0.2 wt. % to about 1.0 wt. % of total composition.

Without wishing to be bound by any theory, it is believed that the mechanism of pseudoplasticity of a silicone-based ink, according to some embodiments, involves the formation of a stable 3D network between treated-silica filler particles and a rheological modifying additive via hydrogen bonding and potential van der Waals interactions.

In other approaches, a more hydrophilic reinforcing filler such as untreated fumed silica may be incorporated into the silicone-based material to impart thixotropy of the silicone material into solid-like network in the absence of applied stress. The mechanism of pseudoplasticity may be attributed to unreacted silanol groups on the silica surface, thereby allowing for particle associations through hydrogen bonding to form an anti-sagging network exhibiting shape retention behavior.

Embodiments described herein encompass a low-temperature stable silicone-based material with the ideal rheology for 3D printing, which may be custom formulated to yield a wide range of physical properties applicable to a variety of fields and industries. For example, the reinforcing filler may be refractive index-matched to impart a 3D silicone structure with transparent optical-grade properties. According to various embodiments described herein, a wide-range of silicone-based 3D structures of varying hardness and stiffness levels may be prepared from silicone-based materials.

In some embodiments, silicone-based inks may be pseudoplastic, non-Newtonian fluids, capable of being deposited in a layer-by-layer pattern during 3D printing.

In some embodiments, the silicone-based ink may include a curing agent. In some approaches, the curing agent may utilize hydrosilylation chemistry during the curing of the 3D structure, such as a platinum curing agent (e.g., Karstedt Pt catalyst), ruthenium curing agent, iridium curing agent, and/or rhodium curing agent. In some approaches, platinum-catalyzed hydrosilylation chemistry (e.g. platinum catalyzed addition of silanes to alkenes) may be used to cure the structured formed with silicone-based inks. In other approaches, ruthenium-catalyzed hydrosilylation chemistry may be used to cure the structures formed with silicone-based inks. In yet other approaches, iridium-catalyzed hydrosilylation chemistry may be used to cure the structures formed with silicone-based inks. In yet other approaches, rhodium-catalyzed hydrosilylation chemistry may be used to cure the structures formed with silicone-based inks.

In some approaches, it is advantageous to use platinum (Pt)-group metal-catalyzed hydrosilylation chemistry because the process does not generate volatile reaction products as compared to condensation cure reactions that produce byproducts such as acetic acid and ethanol. Moreover, these byproducts could deleteriously contribute to some material shrinkage and deviation from the form of the printed 3D structure as deposited.

In some embodiments, the silicone-based ink may include a Pt-group metal curing agent involved in metal catalyzed hydrosilylation chemistry, at a concentration in the range of about 1 to about 1000 ppm, and preferably in a range of about 1 to about 100 ppm, and ideally, 1 to about 50 ppm. In some approaches, the silicone-based ink may include an effective amount of Pt-group metal to initiate a metal-catalyzed hydrosilylation chemistry curing reaction at pre-defined curing conditions, e.g. a pre-defined elevated temperature.

In some embodiments, the silicone-based ink may include an effective amount of an inhibitor for controlling a rate of curing by the curing agent under ambient atmospheric conditions. In some approaches, the inhibitor may be selected based on the curing agent. In some approaches, to maximize the printing time before cure (for example, delay the curing reaction as long as possible), an appropriate choice of a reaction inhibitor relative to the curing agent may be added to inhibit platinum-catalyzed curing chemistry, thereby providing a prolonged pot life duration for extended 3D printing sessions.

In some approaches, in the absence of the reaction inhibitor, the curing mechanism involving the polymerization reaction may proceed rapidly thereby solidifying the printed part within minutes. Thus, a metal-catalyst curing agent (for example Karstedt Pt catalyst), without reaction inhibitor may be undesirable for silicone-based inks involved in the printing of large parts.

In some approaches, the curing agent may induce curing in response to ultraviolet radiation. In other approaches, a curing agent may induce curing in response to free radical chemistry. In yet other approaches, the curing agent may induce curing in response to ionizing radiation. Known curing agents may be used in such approaches.

In some embodiments, the silicone-based ink may include a cross-linking agent as used in cure chemistry. For example, one hydrosilylation cure of siloxanes involves a poly(methylhydrosiloxane) containing additive in which the number of methylhydrosiloxane units along the polymeric or oligomeric chain may be greater than 3 per molecule. In various embodiments, through the implementation of dihydride chain extension chemistry, a silicone-based ink may be formed with very low hardness and stiffness that may be applicable to soft robotics and flexible electronics. In some approaches, a cross linking agent may be hydride terminated chain extension additives, for example, a hydride terminated PDMS-poly(hydrogenmethylsiloxane)(PHMS) copolymer. In other approaches, a short chain vinyl terminated PDMS additive may also be included to impart greater hardness to the cured material.

In some embodiments, the silicone-based inks described herein may be stable at low temperatures. Conventional PDMS-based materials exhibit relatively poor temperature stability beyond −45° C. due to PDMS crystallization. In some approaches, the replacement of PDMS with a random copolymer of PDMS and about 2-6 mole % diphenylsiloxane (DPS) may impart low temperature stability of silicone-based ink. For example, incorporation of the diphenyl moieties of DPS may inhibit crystallization of the PDMS chains at reduced temperature. In other approaches, short chain vinyl-terminated PDMS may be used with additional silica filler to decrease the average molecular weight between crosslinking sites thereby resulting in high hardness and stiffness of the 3D printed structure from the silicone-based ink.

In some embodiments, the silicone-based inks may be formulated to yield two-part materials in predetermined ratios. For example, Part A may include vinyl-terminated poly(dimethylsiloxane)-co-(diphenylsiloxane) macromer, a hydrophobic reinforcing filler, a rheology modifying additive, and a curing agent; and Part B may include a curing agent inhibitor, a crosslinker and an additional vinyl-terminated polydimethylsiloxane-co-diphenysiloxane macromer to create a 10:1 2-part A: B system. In some approaches, Part A may be assembled and then may be stored until use. Part B may be assembled and then stored until use. In other approaches, Part A and Part B may be assembled separately and used immediately.

FIG. 1 shows a method 100 for additive manufacturing with silicone-based ink, in accordance with one embodiment. As an option, the present method 100 may be implemented to construct structures such as those shown in the other FIGS. described herein. Of course, however, this method 100 and others presented herein may be used to form structures for a wide variety of devices and/or purposes which may or may not be related to the illustrative embodiments listed herein. Further, the methods presented herein may be carried out in any desired environment. Moreover, greater or fewer operations than those shown in FIG. 1 may be included in method 100, according to various embodiments. It should also be noted that any of the aforementioned features may be used in any of the embodiments described in accordance with the various methods.

According to one embodiment, the method 100 begins with step 102 involving adding a mixture to a cartridge for additive manufacturing, the mixture comprising a vinyl-terminated polydimethylsiloxane macromer, a hydrophobic reinforcing filler, and a rheology modifying additive. In this and other embodiments, the cartridge may be a nozzle. The mixture may be formed in the nozzle, where one or more of the components is added to the nozzle separately from the other components. A mixer may provide mixing within the nozzle. In another approach, the mixture may be premade and fed to the nozzle.

In some approaches, step 102 may include adding to the mixture, in the cartridge, a curing agent and/or a crosslinking agent. Alternatively, the curing agent and/or crosslinking agent may be part of a premade mixture that is fed through the cartridge.

In yet other approaches, step 102 may include adding to the mixture, in the cartridge, an effective amount of an inhibitor for controlling a rate of curing by the curing agent. Alternatively, the inhibitor may be part of a premade mixture that is fed through the cartridge.

Step 104 of method 100 involves extruding the mixture through the cartridge to form a structure. In various approaches, the presence of a rheology modifying additive imparts pseudoplasticity to the silicone-based ink such that the compression stress of the ink in the cartridge allows the ink to be extruded from the cartridge during 3D printing.

Step 106 of method 100 involves curing the mixture to at least a predefined extent. In various approaches, the 3D printed structure of silicone-based ink may be cured according to the curing agent present in the silicone-based ink. In some approaches, the temperature may be raised in order to initiate curing. In other approaches, UV irradiation may be used to initiate curing of the printed structure. In yet other approaches, free radical chemistry may be used to initiate curing of the printed structure. In various other approaches, curing may be initiated by methods known by one skilled in the art.

In some approaches of method 100, the formed structure may be a three-dimensional structure. In some approaches of method 100, the applied manufacturing is direct ink writing.

In one embodiment, a product of additive manufacturing with a silicone-based ink includes a vinyl-terminated siloxane macromer, a hydrophobic reinforcing filler, a rheology modifying additive, a curing agent, an inhibitor of the curing agent, and a crosslinking agent. In some approaches, the product may be a silicone-based three-dimensional (3D) structure.

In some embodiments, the product of additive manufacturing with silicone-based ink may have features about 100 μm or larger. Based on the ink viscosity smaller features may be created below 100 μm. In some embodiments, the product may have dimensional stability. In other words, the structure formed following 3D printing with silicone-based inks may retain pre-defined dimensions following curing of the structure, for example, there is minimal shrinkage.

In some embodiments, 3D printable silicone-based materials may be prepared with hardness values as low as Shore 10A (see Table 1 Experiments Section below), indicating penetration by the indenter of the durometer. A Shore durometer may be used to provide a measure of hardness in polymer, elastomer, and rubber material in terms of the material's resistance to indentation. The inclusion of dihydride chain extenders may serve to increase the molecular weight of the silicone polymer between crosslinking sites, yielding a material with reduced hardness and stiffness.

Figure 2:
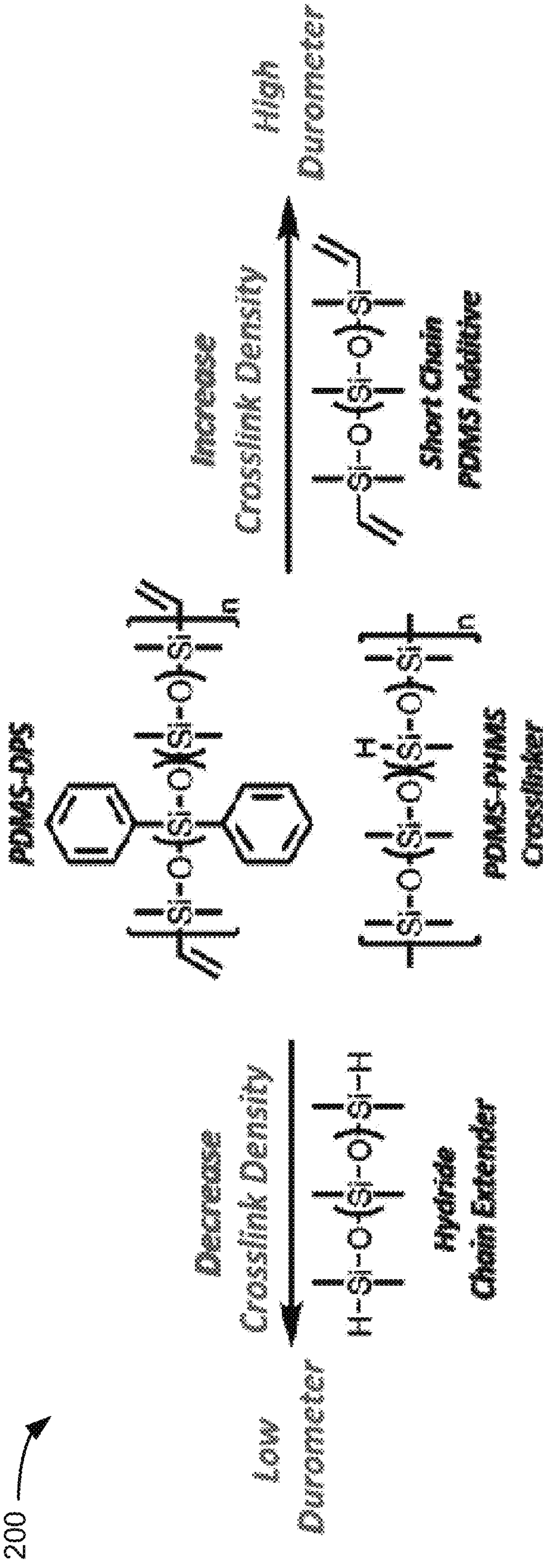
FIG. 2 is a schematic drawing of durometer silicone elastomers, according to various embodiments.

FIG. 2 depicts a structure 200 of variable durometer silicone elastomers, in accordance with one embodiment. As an option, the present structure 200 may be implemented in conjunction with features from any other embodiment listed herein, such as those described with reference to the other FIGS. Of course, however, such structure 200 and others presented herein may be used in various applications and/or in permutations which may or may not be specifically described in the illustrative embodiments listed herein. Further, the structure 200 presented herein may be used in any desired environment.

FIG. 2 is a simplified diagram that describes the formulation of variable durometer silicone elastomers. The core formulation components involved in custom stiffness tuning include a vinyl terminated PDMS-DPS polymer in conjunction with a hydride terminated PDMS-PHMS copolymer crosslinker, other components include silica fillers, rheological additives, inhibitors, and curing agents (for example, Pt catalysts). In some approaches, a reduction in the effective crosslink density and less stiffness (shifting to the left, Low Durometer) may be achieved through the use of hydride terminated chain extension additives. In other approaches, an increase in the effective crosslink density and greater stiffness (shifting to the right, High Durometer) may be achieved through the use of low molecular weight or short chain vinyl terminated PDMS additives, or those additives such as vinyl containing siloxane resins, such as siloxane resins built from M and Q units (MQ resins).

In some embodiments, the direct application of additive manufacturing using silicone-based inks with tunable stiffness may allow engineering of components and parts with specific properties including both low and high potential stiffness. In some approaches, silicone-based materials with differential stiffness may be 3D printed in tandem or simultaneously to generate unique objects with novel properties that are applicable to a wide-range of fields such as soft robotics and stretchable electronics.

Silicone Inks containing Microstructure Particles

In various embodiments a 3D printed hierarchical porous siloxane may be produced by direct ink write (DIW) additive manufacturing utilizing a thixotropic silicone ink, as described herein. In one approach, a nozzle may be loaded with sub-50 micron (μm) liquid-filled siloxane spheres, e.g., liquid-filled particles. In some approaches, the liquid filled in the particles may be substituted with active pharmaceutical ingredients. In some approaches, liquid filled in the particles may be doped with active pharmaceutical ingredients. A structure may be formed using an ink loaded with the liquid-filled particles, where the structure may be tuned to release the active pharmaceutical ingredients (e.g., drugs) from the liquid-filled particles according to a controlled drug release protocol. In other words, in an exemplary approach, the structure allows a controlled release of drugs from the 3D printed device.

In some embodiments, a cellular porosity of a 3D printed structure may be generated by extraction of inter-cellular fluid with specific drying techniques, e.g., supercritical carbon dioxide ($CO_2$), thereby forming a 3D printed structure with macro and micro scale porosity introduced to the structure using the AM process and siloxane spheres, respectively.

In various approaches, liquid-filled siloxane microspheres (e.g., liquid-filled particles) may be fabricated by two methods; a) dual phase separation of crosslinkable silicone resin from a THF/oil co-solvent, b) a double emulsion template involving emulsified and cured in a surfactant stabilized aqueous solution. Applying these methods, according to various approaches, DIW printed structures using silicone inks may have variable porosity, controlled release properties, etc.

Figure 9A:
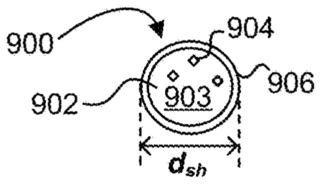
FIG. 9A illustrates a schematic drawing of a core-shell microsphere, according to one embodiment.

FIG. 9A depicts a schematic drawing of a core-shell microsphere 900, in accordance with one embodiment. As an option, the present core-shell microsphere 900 may be implemented in conjunction with features from any other embodiment listed herein, such as those described with reference to the other FIGS. Of course, however, such a core-shell microsphere 900 and others presented herein may be used in various applications and/or in permutations which may or may not be specifically described in the illustrative embodiments listed herein. Further, the core-shell microsphere 900 presented herein may be used in any desired environment.

In one embodiment, as shown in FIG. 9A, a core-shell microsphere 900 includes a polyorganosiloxane shell 906 and a core 902 inside the shell 906, the core 902 having a carrier 903 and at least one component 904, where the at least one component 904 may be configured to be released post processing. In one approach, the carrier 903 may be a liquid having at least one component that may be released post processing. For example, and not meant to be limiting in any way, the carrier may be an oil that is immiscible with a siloxane resin, e.g., mineral oil. In one approach, the carrier may be a long chain hydrocarbon.

In one approach, the carrier 903 may be tuned to the solubility of the at least one component 904 of the core 902 according to a predefined characteristic for the at least one component to be released under predefined conditions.

In some approaches, the carrier 903 may be a mixture tuned to the solubility of the at least one component 904 of the core 902 of the core-shell microsphere 900.

In another approach, the carrier may be a solid that dissolves in body fluid, for example, the carrier may melt at a body temperature (e.g., 32° C. to 37° C.), and then the component included with the now-melted carrier in the core may be released.

In various approaches, the at least one component 904 included with the carrier 903 in the core 902 may be a material that includes at least one of the following, a compound for pharmaceutical application, a monomer, an oligomer, a polymer, a catalyst, or a combination thereof. In some approaches, the compound for pharmaceutical application may be timed-release, control-release, etc. drug. For example, and not meant to be limiting in anyway, the compound may be an antibiotic, pain-reliever, etc.

In some approaches, an average diameter $d_{sh}$ of the polyorganosiloxane shell 906 may be in a range of greater than about 1 μm to less than about 100 μm. In some approaches, the average diameter $d_{sh}$ of the polyorganosiloxane shell 906 may be in a range of greater than about 10 μm to less than about 30 μm. In various approaches, the diameter of the polyorganosiloxane shell may be equal to the diameter of the core-shell microsphere.

In one approach, the polyorganosiloxane shell may include polydimethylsiloxane diphenylsiloxane and a reinforcing filler. In one approach, the reinforcing filler may be a fumed silica. In another approach, the reinforcing filler may be a trimethylsiloxysilicate graft polydimethylsiloxane.

Figure 9B:
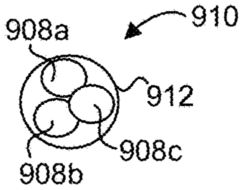
FIG. 9B illustrates a schematic drawing of a core-shell microsphere, according to one embodiment.

In some approaches, the shell of the core-shell microspheres may be defined as a solid that creates an exterior surface of the microspheres. In some approaches, the shell may be independent of whether the microsphere has a single, double, multiple, etc. core(s) within the microsphere. In other words, as shown in FIG. 9B, a single shell 912 of the microsphere 910 may encapsulate more than one core 908*a*, 908*b*, 908*c*, e.g., a core-shell microsphere 910 may include 3 cores inside a single shell. In some approaches, a core-shell microsphere may be a micro-structured particle.

Figure 9C:
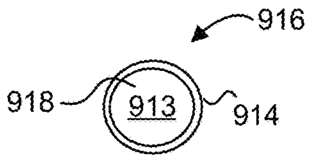
FIG. 9C illustrates a schematic drawing of a core-shell microsphere, according to one embodiment.

In one embodiment, as shown in FIG. 9C, a core-shell microsphere 916 may be a porogen. In one approach, the shell 914 of the core-shell microsphere 916 encapsulates a core 918 that includes a liquid 913 having a low boiling point. In one approach, a boiling point of the liquid 913 of the core 918 may be in a range of about 50° C. to about 200° C.

In one embodiment, silicone inks for DIW processes may be prepared to contain microstructure particles, core-shell microspheres, microballoons, etc. In some approaches, the microstructure particles are oil-filled particles fabricated from a dual phase separation emulsion template.

Figure 10A:
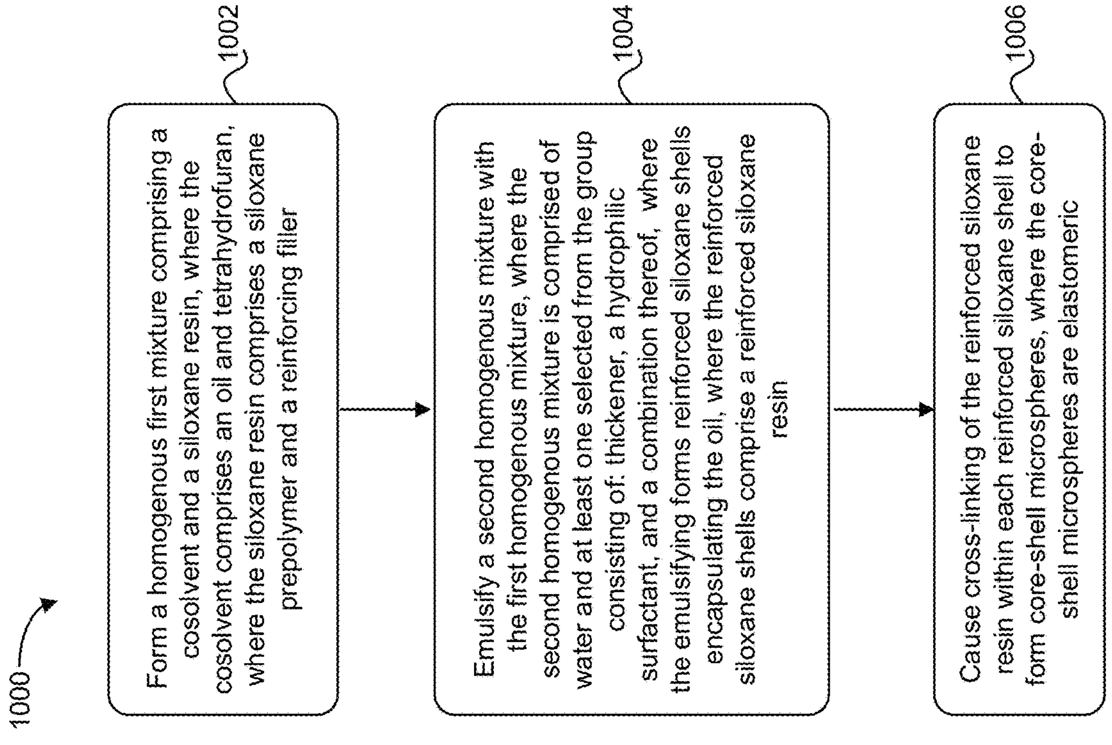
FIG. 10A is a flow chart of a method, according to one embodiment.

FIG. 10A shows a method 1000 for forming a plurality of core-shell microspheres, in accordance with one embodiment. As an option, the present method 1000 may be implemented to construct structures such as those shown in the other FIGS. described herein. Of course, however, this method 1000 and others presented herein may be used to form structures for a wide variety of devices and/or purposes which may or may not be related to the illustrative embodiments listed herein. Further, the methods presented herein may be carried out in any desired environment. Moreover, greater or fewer operations than those shown in FIG. 10A may be included in method 1000, according to various embodiments. It should also be noted that any of the aforementioned features may be used in any of the embodiments described in accordance with the various methods.

Method 1000 may begin with step 1002 of forming a homogenous first mixture that includes a cosolvent and a siloxane resin. In one approach, the cosolvent includes an oil and tetrahydrofuran. In one approach, the siloxane resin includes a siloxane prepolymer and a reinforcing filler.

In some approaches, particles shells are composed of polydimethysiloxanediphenylsiloxane (PDMS-DPS) reinforced by a dissolvable filler, for example, mono (M)- and tetra (Q)-functional siloxane units (MQ copolymers), MT resin, MDQ resin, or any combination thereof, e.g., trimethylsiloxysilicate graft polydimethylsiloxane (MQ-PDMS). In another approach, the reinforcing filler may be fumed silica. In yet other approaches, the filler may be calcium carbonates, and other fillers known to those in the art. The composite may yield a reinforced siloxane with little change in viscosity attributed to the reinforcing filler. In one approach, the material may be fabricated in to shells by its separation from a mineral oil and tetrahydrofuran (THF) cosolvent solution that is sequentially emulsified into a surfactant loaded aqueous phase.

Step 1004 includes emulsifying a second homogenous mixture with the first homogenous mixture, as formed in step 1002. The second homogenous mixture may include water and a thickener and/or a hydrophilic surfactant. The second homogenous mixture may be an aqueous phase. In one approach, thickeners as known by one skilled in the art may be included in the second homogenous mixture. For example, the thickener may include polyvinyl alcohol, polyethylene glycol, polysaccharides, etc. or a combination thereof. In one approach, hydrophilic surfactants as known by one skilled in the art may be included in the second homogenous mixture. For example, a hydrophilic surfactant having functional segments may include a siloxane, an alkyl, a polyether, or a combination thereof. In one approach, the hydrophilic surfactant may be Tween, Span, poloxamer, etc. or a combination thereof.

In one approach, the emulsifying may form reinforced siloxane shells encapsulating the oil, where the reinforced siloxane shells include a reinforced siloxane resin. Mechanistically, in one approach, a concentration gradient drives a separation of THF into the aqueous phase which yields a phase separation between the oil and siloxane resin.

Step 1006 includes causing cross-linking of the reinforced siloxane resin within each reinforced siloxane shell to form core-shell microspheres. In various approaches, the core-shell microspheres are elastomeric. In one approach, thermal crosslinking of the siloxane resin yields dispersed unique core-shell microspheres, with siloxane shells that encapsulate the oil phase. In some approaches, the temperature for thermal curing the siloxane resin may be in a range of room temperature to about 70° C.

In one approach, ultraviolet (UV) crosslinking of the siloxane resin of the shells may yield unique elastomeric core-shell microspheres having a liquid core encapsulated with a siloxane shell.

In some approaches, the core-shell microspheres may be fabricated by sequential preparation. For example, for a core-microsphere having three different drugs that will be released at different times, the process may include: prepare the core drug mixture 1, change the shell adapted for release of drug 1; prepare core drug mixture 2, change the shell adapted for release of drug 2; prepare core drug mixture 3, change the shell adapted for release of drug 3. Preferably, the core-shell microspheres may include three different shells in the same matrix having different rates of drug release. In some approaches, depending on the silicone material of the shell, drugs may be released at a variable rate.

In various approaches, the micro-structured core-shell microsphere as described may have greater use as a carrier for active pharmaceutical ingredients for targeted drug delivery applications.

In one approach, the liquid in the core of the core-shell microsphere includes a perfluorocarbon (PFC). In one embodiment, alternative and novel perfluorocarbon (PFC) filled siloxane spheres having the same shell composition may be fabricated by a different approach through a PFC/PDMS/aqueous double emulsion.

Figure 10B:
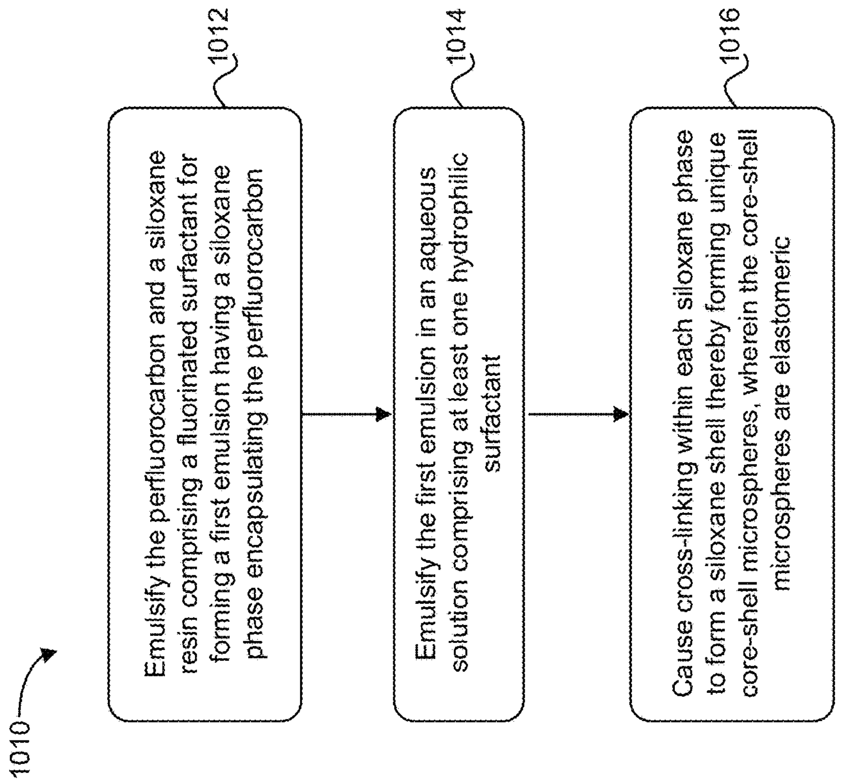
FIG. 10B is a flow chart of a method, according to one embodiment.

FIG. 10B shows a method 1010 for forming a plurality of core-shell microspheres, in accordance with one embodiment. As an option, the present method 910 may be implemented to construct structures such as those shown in the other FIGS. described herein. Of course, however, this method 1010 and others presented herein may be used to form structures for a wide variety of devices and/or purposes which may or may not be related to the illustrative embodiments listed herein. Further, the methods presented herein may be carried out in any desired environment. Moreover, greater or fewer operations than those shown in FIG. 10B may be included in method 1010, according to various embodiments. It should also be noted that any of the aforementioned features may be used in any of the embodiments described in accordance with the various methods.

Method 1010 may begin with step 1012 that includes emulsifying a liquid having a low boiling point, e.g., a perfluorocarbon, and a siloxane resin including a fluorinated surfactant. This forms a first emulsion having a siloxane phase encapsulating the liquid (e.g., perfluorocarbon (PFC)). In some approaches, a surfactant having a fluorinated segment and a siloxane, alkyl, polyether or a combination thereof segment is used to stabilize the emulsion during the process. In one approach, PFC-filled microspheres may be fabricated by emulsifying a PFC into a low viscosity siloxane resin containing a fluorinated surfactant.

In some approaches, perfluorocarbon liquids having a boiling point in a range of 50° C. to 200° C. are preferable.

In some approaches, the siloxane resin includes a siloxane having a viscosity less than 2000 centiStokes (cSt). Preferably, the siloxane resin includes a siloxane having a viscosity less than 1000 cSt. In an exemplary approach, the siloxane resin includes a siloxane having a viscosity of about 800 cSt. For example, and not meant to be limiting, the siloxane resin may include polydimethylsiloxane diphenylsiloxane (PDMS-DPS).

Step 1014 includes emulsifying the first emulsion in an aqueous solution comprising at least one hydrophilic surfactant. In one approach, a primary PFC/siloxane emulsion may be emulsified into an aqueous solution containing hydrophilic surfactants.

Step 1016 includes causing cross-linking within each siloxane phase to form a siloxane shell thereby forming dispersed unique core-shell microspheres, wherein the core-shell microspheres are elastomeric. In one approach, the dispersed siloxane in the secondary emulsion may be thermally crosslinked, thus yielding elastomeric particles, with siloxane shells that encapsulate the PFC phase.

In various approaches, particle size distribution may be controlled as a function of emulsification parameters such as aqueous surfactant concentration and emulsification shear, as well understood by one skilled in the art.

PFC-filled microspheres may have single or multiple cores depending on the interparticle PFC volume, as shown in FIG. 9B.

In some approaches, the microstructured microsphere as described herein may have preferred use as a porogen for siloxane inks due to its simple post processing in which the core is evaporated out of the shell, compared to conventional methods involving solvent exchange and critical point extraction for removal of oil-filled microspheres.

In one embodiment, a plurality of prefabricated liquid-filled microspheres may be loaded into a siloxane ink with ideal rheology for 3D printing. In some approaches, the liquid-filled particles may be formulated to achieve a broad range of encapsulated liquid volume.

Figure 9D:
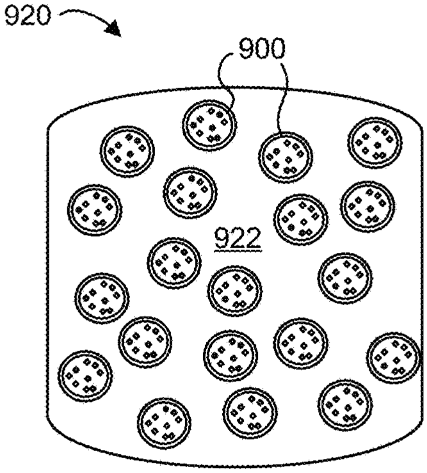
FIG. 9D illustrates an ink having core-shell microspheres, according to one embodiment.

FIG. 9D depicts a schematic drawing an ink 920, in accordance with one embodiment. As an option, the present ink 920 may be implemented in conjunction with features from any other embodiment listed herein, such as those described with reference to the other FIGS. Of course, however, such an ink 920 and others presented herein may be used in various applications and/or in permutations which may or may not be specifically described in the illustrative embodiments listed herein. Further, the ink 920 presented herein may be used in any desired environment.

In one embodiment, a silicone ink 920 as described herein may include a mixture 922 including vinyl-terminated diphenyl siloxane macromer, a treated silica hydrophobic reinforcing filler, a rheology modifying additive, and a plurality of core-shell microspheres 900. In one approach, as described herein, an average diameter $d_{sh}$ of core-shell microspheres 900 may be in a range of greater than about 1 μm to less than about 100 μm. In one approach, an average diameter $d_{sh}$ of core-shell microspheres 900 is in a range of greater than about 10 μm to less than about 30 μm.

In various approaches, the ink 920 includes core-shell microspheres 900 that include a carrier 903 and at least one component 904 that may be released post processing, e.g., after printing a structure with the ink. In some approaches, the component may be a compound for a pharmaceutical application. In one approach, the component may be a monomer, oligomer, polymer, or a combination thereof. In one approach, the component may be a catalyst. In various approaches, the component in the core of the core-shell microsphere may be combination of components.

Figure 9E:
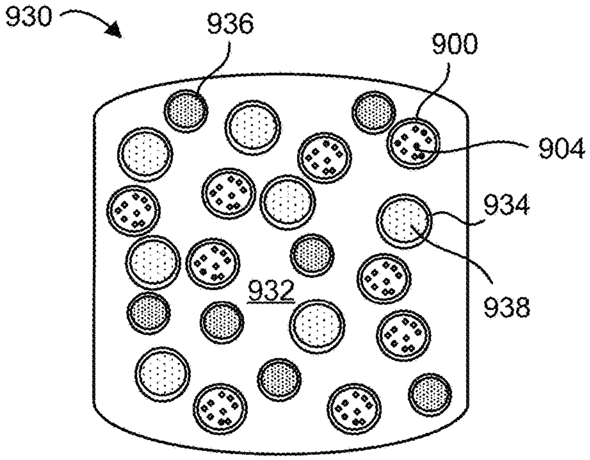
FIG. 9E illustrates an ink having core-shell microspheres, according to one embodiment.

In one approach, as shown in FIG. 9E, the ink 930 may include a mixture 932 of ink components and a mixture of core-shell microspheres 900, 934, 936. In one approach, the at least one component 904 of one core-shell microsphere 900 may be different from at least one component 938 of a second core-shell microsphere 934. In one approach, the at least one component of the first core-shell microsphere may configured to be released from the first core-shell microsphere at a first time, and the at least one component of the second core-shell microsphere may be configured to be released from the second core-shell microsphere at a second time. In one approach, time of the released component from the first core-shell microsphere may be different from the time of the released component from the second core-shell microsphere.

In one approach, a core-shell microsphere may include a single ingredient in the core for controlled drug release. In one approach, a core-shell microsphere may include multiple ingredients in the core having different rates of drug release. For example, drug A may be rapidly released, drug B may be released at a slower rate, and drug C may be released at the end of a defined program. In one approach, the various rates of release of different ingredients may be based on the material composition of the shell.

For example, and not meant to be limiting in any way, an ink may have a population of core-shell particles that are configured to release a pain-reliever within the first 24 hours following implantation of the 3D printed siloxane-core-shell microsphere part, and an ink may also have a population of different core-shell microspheres that are configured to release an antibiotic during an interval of 12 hours to 36 hours following implantation of the 3D printed siloxane-core-shell microsphere part.

In some approaches, as described herein, the ink with the core-shell microspheres may be stable without crystallinity at temperatures down to about −150° C.

Figure 9F:
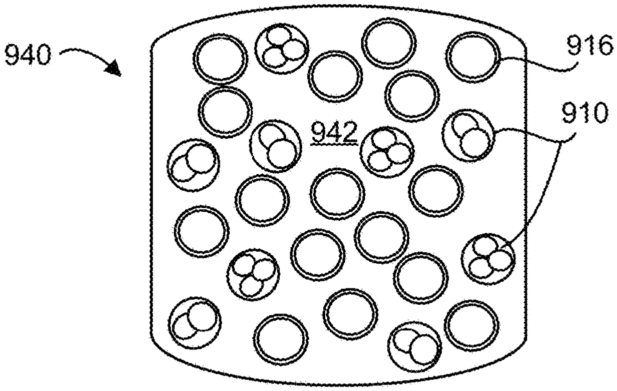
FIG. 9F illustrates an ink having core-shell microspheres, according to one embodiment.

In one approach, as shown in FIG. 9F, the ink 940 may include a mixture of ink components 942 as described herein and a plurality of core-shell microspheres 910, 916 that are porogen, pore-forming, etc. core-shell microspheres. The ink may include a mixture of core-shell microspheres 910. 916 that include core-shell microspheres having single shell encapsulating multiple cores (as illustrated in FIG. 9B) and core-shell microspheres 916 having a single shell encapsulating a single core (as illustrated in FIG. 9C).

In one approach, the ink may be used to form a monolith structure. In one approach the ink may be used to form a thin film. In one approach, the ink may be used to form a structure by injection molding. As would be understood by one skilled in the art, the ink may be used to form a structure using methods generally understood in the art.

Figures 11A, 11B:
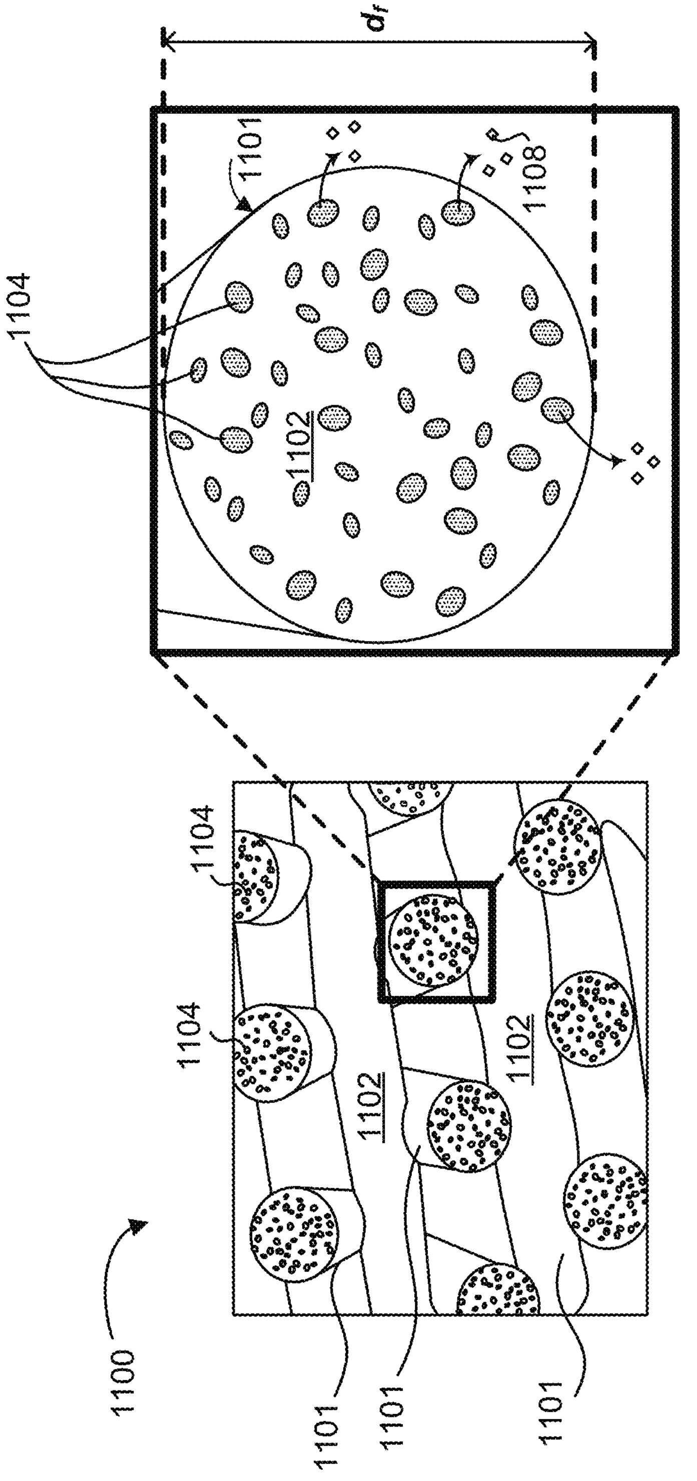
FIG. 11A is a schematic drawing of a three-dimensional silicone-based structure, according to one embodiment.
FIG. 11B is a schematic drawing of a portion of a three-dimensional silicone-based structure of FIG. 11A, according to one embodiment.

FIG. 11A depicts a schematic drawing a structure 1100, in accordance with one embodiment. As an option, the structure 1100 may be implemented in conjunction with features from any other embodiment listed herein, such as those described with reference to the other FIGS. Of course, however, such a structure 1100 and others presented herein may be used in various applications and/or in permutations which may or may not be specifically described in the illustrative embodiments listed herein. Further, the structure 1100 presented herein may be used in any desired environment.

In one embodiment, a product of additive manufacturing may be fabricated with a silicone-based ink having core-shell microspheres. The product may be a silicone-based three-dimensional (3D) structure 1100. The structure 1100 may have a plurality of continuous filaments 1101, and includes a material 1102 of vinyl-terminated siloxane macromer, a hydrophobic reinforcing filler, a rheology modifying additive, and a plurality of core-shell microspheres 1104.

The product may be a part, a structure, etc. In some approaches, the 3D printed silicone-based structure 1100 may be formed in a geometric shape. For example, as shown in FIG. 11A, the 3D printed structure is a log-pile formation.

In one approach, as shown in FIG. 11B illustrating a magnified view of a cross-section of a filament 1101, where an average diameter $d_f$ of the filaments 1101 of the three-dimensional structure 1100 may be greater than about 100 μm. A ratio of an average diameter $d_{sh}$ of the shell of the core-shell microspheres 1104 to the average diameter $d_f$ of the filaments 1101 may be in a range of greater than 1:100 to less than 3:4. In preferred approaches, a ratio of the average diameter of core-shell microspheres to the average diameter of the filaments may be 1:20 diameter of core shell microspheres to diameter of the filaments.

In various approaches, each filament may have a cross-sectional diameter relative to the nozzle of the additive manufacturing (e.g., DIW) technique used to print the structure. Part (b) is a magnified view of a cross-section view of one filament of the structure 1100. As shown as an example only, a diameter $d_f$ of a filament may be in a range of 150 μm for a filament that is extruded through a 250 μm nozzle. The diameter $d_f$ of a filament may be relative to the diameter of the extrusion nozzle used to form the filament.

In various approaches, the core-shell particles 1104 of the material 1102 of the filaments 1101 may have an average diameter in a range of about 10 μm to about 30 μm. In some approaches, the core-shell particles of the 3D printed structure have the same properties of the core-shell structures in the ink that was extruded to form the 3D printed part. In one approach, as illustrated in FIG. 11B of the magnified view of the cross-section of a filament 1101 of the structure 1100, the core-shell microspheres 1104 of the 3D printed silicone-based structure include a carrier and at least one component 1108 that may be released (as shown by the arrow out of the core-shell microsphere 1104 and the filament 1101) post processing of the 3D printed silicone-based structure 1100.

In some approaches, the 3D printed silicone-based part includes core-shell particles that include at least one component that may be a material of the following: a component for pharmaceutical application, a monomer, an oligomer, a polymer, a catalyst, or a combination thereof. In some approaches, the 3D printed silicone-based part may include populations of different core-shell microspheres, where one population of core-shell microspheres release a component from the part at a first time, and a population of different core-shell microspheres release a different component from the part at a second time. In one approach, the first time and the second time may be different. In one approach, the first time and second time are the same.

In one approach, an ink may include multiple types of core-shell microspheres that are distinguished by the content of the core of each core-shell particle, and the silicone-based shell moderate the speed of the internal phase release from the core of the core-shell microspheres. For example, a compound of these different core-shell microspheres, e.g., A, B and C, may have a controlled release of Microsphere A will release fast, Microsphere B will release slower, and Microsphere C will release the slowest. As a composite of microspheres in a 3D printed part, the microspheres may be fabricated differently, and the release rates will be controlled according to application.

In one approach, active pharmaceutical ingredients may be added to the liquid phase of the liquid-filled core-shell microspheres. The resulting 3D printed devices that include the liquid-filled particles as described herein may be utilized to release active ingredients in a selective and controlled manner. For example, without wishing to be limiting in any way, a 3D printed transdermal implant may be formulated and printed so that antibacterial ingredients may be release at a prescribed release rate specifically at the dermal junction. Such approaches may increase implant success and patient comfort.

In contrast to conventional technology, various embodiments described herein describe active pharmaceutical ingredients that may be entirely contained within a shell within the liquid-filled particle, and thus, the 3D printed implant functions without a secondary coating.

Moreover, in some approaches, a prefabricated particle shell may be used to determine particle characteristics, such as a release rate of active pharmaceutical ingredients, a trigger for release of active pharmaceutical ingredients, a schedule of triggers of different active pharmaceutical ingredients, etc.

In one embodiment, a product may include core-shell microspheres where the carrier component of the core may be released from the part post processing (e.g., post 3D printing and curing), and thereby creating a pore in the product. The product may be a 3D printed silicone-based part, structure, etc. Following release of the carrier component from the core-shell microspheres, the product may be a porous 3D printed silicone-based part.

In various approaches, the liquid in the core of the core-shell microspheres may be removed by techniques known in the art. For example, the 3D printed part may be dried to evaporate the liquid, supercritically dried to evaporate the liquid, etc. In one approach, the liquid may be volatile, such that the liquid evaporates post processing.

In various embodiments, the mechanism described herein may allow greater versatility for bulk material to fit specific critical characteristics (requirements) of a desired implant, for example, hardness, durability, etc.

Figure 12:
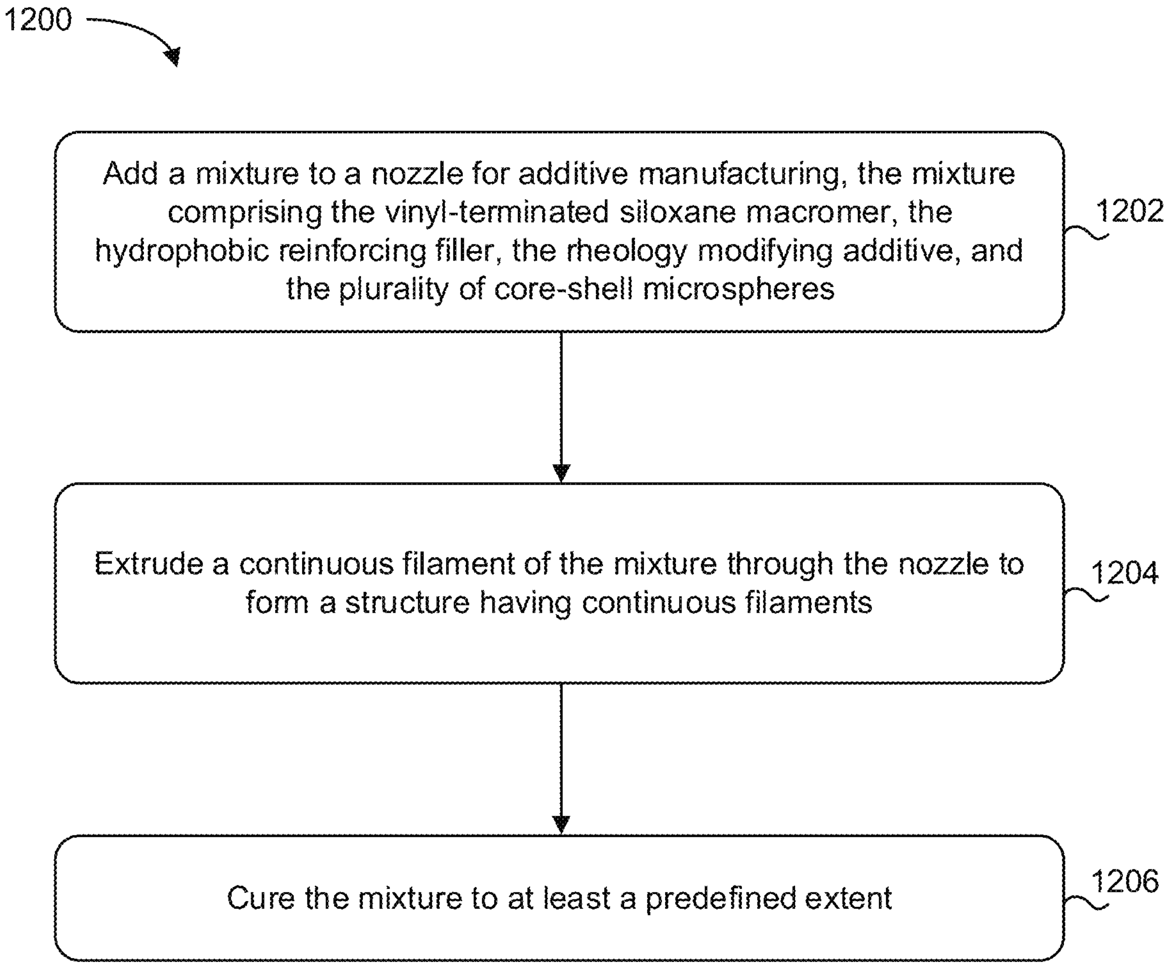
FIG. 12 is a flow chart of a method, according to one embodiment.

FIG. 12 shows a method 1200 for a product of additive manufacturing with a silicone-based ink having core-shell microspheres, in accordance with one embodiment. As an option, the present method 1200 may be implemented to construct structures such as those shown in the other FIGS. described herein. Of course, however, this method 1200 and others presented herein may be used to form structures for a wide variety of devices and/or purposes which may or may not be related to the illustrative embodiments listed herein. Further, the methods presented herein may be carried out in any desired environment. Moreover, greater or fewer operations than those shown in FIG. 12 may be included in method 1200, according to various embodiments. It should also be noted that any of the aforementioned features may be used in any of the embodiments described in accordance with the various methods.

Method 1200 may begin with step 1202 of adding a mixture to a nozzle for additive manufacturing. The mixture may include the vinyl-terminated siloxane macromer, the hydrophobic reinforcing filler, the rheology modifying additive, and the plurality of core-shell microspheres. In one approach, the components of the mixture may be mixed before adding the mixture to the nozzle. In one approach, at least one component of the mixture may be added to the mixture in the nozzle.

In various approaches, the mixture is an ink. In one approach, the plurality of core-shell microspheres may be added to the ink before adding the ink to the nozzle. In one approach, the plurality of core-shell microspheres may be added to the ink in the nozzle before extrusion of the ink.

Step 1204 includes extruding a continuous filament of the mixture through the nozzle to form a structure having continuous filaments. In one approach, ink loaded with liquid-filled core-shell microspheres may be extruded from a nozzle to print a 3D structure. In one approach, the formed structure is a 3D structure. In one approach, the additive manufacturing is direct ink writing (DIW).

Step 1206 includes curing the mixture to at least a predefined extent. Techniques generally understood in the art and as presented herein may be used to cure the material of the 3D printed silicone-based part having core-shell microspheres therein. In one approach, the 3D structure may be cured and then sequentially post processed.

Post processing techniques may depend on the application of the 3D printed silicone-based microsphere part. In some approaches, the components of the core-shell microspheres may be released post processing. In some approaches, the carrier of the core-shell microspheres may be released post processing.

In various embodiments, the ability to 3D print the ink loaded with liquid-filled particles produces devices by such proven techniques such as injection molding, DIW, etc. and thereby allows better tailoring of the device to individual patients, or patient groups, and a streamlined adoption by commercial entities.

In one embodiment, liquid filled particles may be used as a poreformer in a siloxane ink. Post processing of structures printed with the ink loaded with liquid-filled particles as described herein allows removal of the liquid phase of the particles while the cellular structure is maintained and uncompromised by the removal of the liquid from the particles. The resulting structure may have a closed cell porous network where a void (e.g., no liquid, no solid, etc.) occupies the space previously occupied by the liquid in the particles, and further the void space is defined by the interior of the shell of the particle. Applications of this closed cell material may include, for example without wishing to be limiting in any way, low-density foams, energy absorbing cushions for aerospace, automotive applications, etc.

Experiments

Material and Methods

A poly(diphenylsiloxane-dimethylsiloxane) copolymer (10,000 cSt, ca. 5.5 mole % diphenylsiloxane), PLY3-7560, was obtained from NuSil Technology (Bakersfield, CA). Platinumdivinyltetramethyldisiloxane complex (Karstedt's catalyst, low color, ca. 2%) in xylene was supplied by Gelest, Inc (Morrisville, PA). (SIP6831.2LC), as were DMS-H11 (hydride terminated PDMS, 10 cSt), HMS-053 (trimethyl terminated [4-6% methylhydrosiloxane] dimethylsiloxane, 1000 cSt), DMS-V05 (divinyl PDMS, 8 cSt), and HMS-H271 (hydride terminated [30% methylhydrosiloxane] dimethylsiloxane copolymer, 60 cSt). 1-ethynyl-1-cyclohexanol (ETCH) was supplied by Sigma-Aldrich (St. Louis, MO). Bluesil™ Thixo Add 22646 was supplied by Elkem Silicones (Oslo, Norway). Aerosil® R812S and Sipernat® D13 were supplied by Evonik Industries (Essen, Germany), SIS 6962.1M30 was obtained from Gelest, and Cabosil EH5 was obtained from Cabot Corp (Boston, MA). All materials were used as-is without further purification. Formulations were prepared using a Flacktek DAC 150.1 FVZ-K SpeedMixer™ (Landrum, SC) for compounding. Catalyst cure temperatures and ink thermal response values were measured using a TA Instruments Discovery DSC (New Castle, DE) differential scanning calorimeter using Tzero® aluminum sample pans (NDS Surgical Imaging, Sunnyvale, CA). Yield stress, viscosity, pot life measurements, and cure profiles were obtained with a TA Instruments AR2000EX rheometer equipped with a cross-hatched 25 mm Peltier parallel plate under a 1 mm sample gap spacing.

Once formulated, all silicone-based inks were filtered (pressurized air, 90 psi) through a Swagelok 140 μm mesh filter (Solon, OH) into 30 mL syringe barrels (Nordson EFD Optimum, East Providence, RI) and centrifuged (Nordson EFD ProcessMate 5000) to eliminate entrapped air. A flat-ended piston was inserted to seal the rear of the syringe; whereas, the syringe tip was equipped with a smooth-flow tapered nozzle (250 μm inner diameter) via luer-lock. The syringe was attached to a positive-displacement dispenser (Ultra 2800, Nordson EFD), which supplied the appropriate displacement to extrude ink through the nozzle. The syringe system was subsequently affixed to the z-axis of a custom Aerotech air-bearing gantry xy open frame movement stage, which was controlled via an A3200 controller through an Aerotech A3200 CNC operator interface (v5.05.000) (Aerotech Consumer Aerospace, Pittsburgh, PA.0. G-code instructions were programmed and run through the controller software to generate continuous FCT lattice structures with a 50% effective density. The lattice structures were printed onto silicon wafers with each layer of parallel filaments being printed orthogonal to the previous layer, yielding an FCT structural arrangement. The printed lattices were cured in a Yamato ADP300C vacuum drying oven (Yamato Scientific America, Inc, Santa Clara, CA).

Shore hardness values were obtained by preparing solid "pucks" of silicone material that were cured at 150° C. for 12-16 hours. Durometer values were measured at several different locations with a PTC Instruments Model 408 Type A Durometer (Los Angeles, CA). Printed lattice structures were sectioned with a razor blade and cross-sectional images were obtained with a Zeiss SteREO Discovery.V12 microscope (Zeiss, Dublin, CA) equipped with an Axiocam ICc 5 camera and analyzed with AxioVision software to measure the diameters of the printed filaments, individual layer heights, and total heights of the printed FCT lattices.

Example Preparation of MD-10A Silicone-Based Ink

A Flacktek Max 100 cup was charged with NuSil PLY3-7560 silicone polymer (24.6 g), platinum catalyst (4 ppm), and inhibitor (ETCH, 400 ppm); the components were mixed with a Flacktek DAC 150.1 FVZ-K SpeedMixer™ at 3500 rpm for 20 seconds. Aerosil® R812Sfumed silica (4.2 g) was subsequently added to the mixture and mixed at 3500 rpm for 20 seconds; the sides of the cup were scraped, and the blend was speed-mixed again under the same conditions. Bluesil™ Thixo Additive 22646 (0.3 g) was added to the mixture, followed by speed-mixing at 3500 rpm for 20 seconds. Lastly, Gelest HMS-H271 (0.221 g) and Gelest DMS-H11 (0.644 g) were added and speedmixed into the blend at 3500 rpm for 20 seconds. The sides of the cup were scraped, and the dispersion blend was speed-mixed again under the same conditions, yielding a viscous translucent polysiloxane ink.

As shown in Table 1, a 3D printable silicone-based ink was prepared with a reduced silica filler loading (14 wt. % HMDZ-treated silica) and cured using 0.75 equivalents (hydride:vinyl) of a dihydride chain extender and 0.75 equivalents of silane crosslinker, which was sufficient to decrease the measured durometer to Shore 10A, (named "modified durometer 10A" or MD-10A).

Evidence of Pseudoplasticity

Analysis of shape retention behavior may be used to evaluate the relationship between properties of silicone-based ink materials. In brief, using a model of Hershel-Bulkley material moving through a cylindrical nozzle, an extruded core material having properties characteristic of an unyielded silicone-based ink based may be subjected to beam deflection analysis. Equation 1 shows the relationship of the elastic behavior of an ink to a desired beam deflection, in which y represents the specific weight of an ink and s represents the beam length (L) to strand diameter (D) ratio, LID.

$$G' \geq 1.4\gamma s^4 D \qquad \text{Equation 1}$$

According to Equation 1, the 3D printable silicone-based inks may possess G' values several orders of magnitude higher than that recommended for a strand deflection of ≤0.05D. Thus, in some approaches, the deposition speed may be tuned to print lower G' inks for 3D printed architectures. Moreover, in come approaches, custom silicone-based ink formulations may support higher density fillers for 3D printed architectures.

Figure 3A:
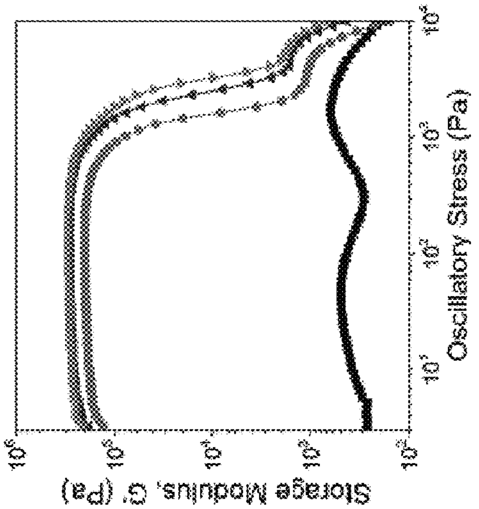
FIG. 3A is a plot of oscillatory stress of storage modulus values for silicone-based inks, according to various embodiments.

FIG. 3A shows the oscillatory stress (Pa, x-axis) of storage modulus (G', y-axis) values for silicone-based inks containing various levels of rheological additive. Yield stress was defined as the oscillatory stress corresponding to 90% of the storage modulus plateau. Increasing the rheological additive content led to an increase in ink yield stress to 410 Pa for an ink containing 0.25 wt. % of a rheological additive (●), 515 Pa for 0.50 wt. % of a rheological additive (▲), and 540 Pa for 1.0 wt. % of a rheological additive (▼) as the degree of pseudoplasticity increased. In the absence of a rheological modifier (■), no pseudoplasticity was observed; instead, the measured storage modulus (G') was always less than that of the loss modulus (G"). However, when the rheological additive was added in the presence of treated silica filler, a highly pseudoplastic material with a large yield stress was obtained.

Figure 3B:
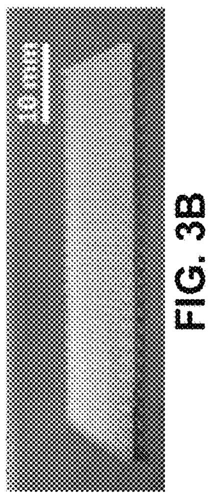
FIG. 3B is a lattice 8-layer structure formed by a silicone-based ink with rheological additive, according to one embodiment.
Figure 3C:
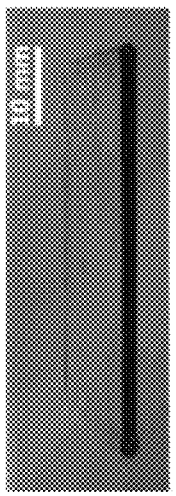
FIG. 3C is a lattice 8-layer structure formed by a silicone-based ink without rheological additive, according to one embodiment.

FIGS. 3B and 3C show a lattice 8-layer structure formed by 3D printing with a silicone-based ink with 1.0 wt. % rheological additive (FIG. 3B) and with silicone-based ink without rheological additive (G">G') (FIG. 3C). Mechanistically, without wishing to be bound by any theory, it is

TABLE 1

3D printable MD-XA silicone inks formulations details.

| Components | MD-10A | MD-25A | MD-45A | MD-55A | MD-60A | MD-70A |
|---|---|---|---|---|---|---|
| NuSil PLY3-7560 | 82% | 81.20% | 76.50% | 71.50% | 67% | 56% |
| Gelest DMS-V05 | — | — | 0.50% | 3.50% | 5% | 9.50% |
| Karstedt's Catalyst | 4 ppm | 4 ppm | 4 ppm | 4 ppm | 4 ppm | 4 ppm |
| ETCH[a] | 400 ppm | 400 ppm | 400 ppm | 400 ppm | 400 ppm | 400 ppm |
| Aerosil ® R812S | 14% | 18% | 12% | 12% | 12% | — |
| Sipemat ® D13 | — | — | 10% | 12% | 15% | 33.50% |
| Bluesil ™ Thixo Additive 22646 | 1% | 0.60% | 1% | 1% | 1% | 1% |
| Gelest DMS-H11 | 0.875 eq.[b] | — | — | — | — | — |
| Gelest HMS-H271 | 0.75 eq.[b] | 1 eq.[b] | 2 eq.[b] | 2 eq.[b] | 2 eq.[b] | 2 eq.[b] |
| Shore A Durometer | 10A | 25A | 45A | 55A | 60A | 70A |

[a]1-ethynyl-1-cyclohexanol.

[b]Equivalents are per each equivalent reactive vinyl group within each formulation.

believed the pseudoplasticity was due to the formation of a stable three-dimensional network between silica filler particles and the rheological additive via hydrogen bonding and potential van der Waals interactions.

Figure 3D:
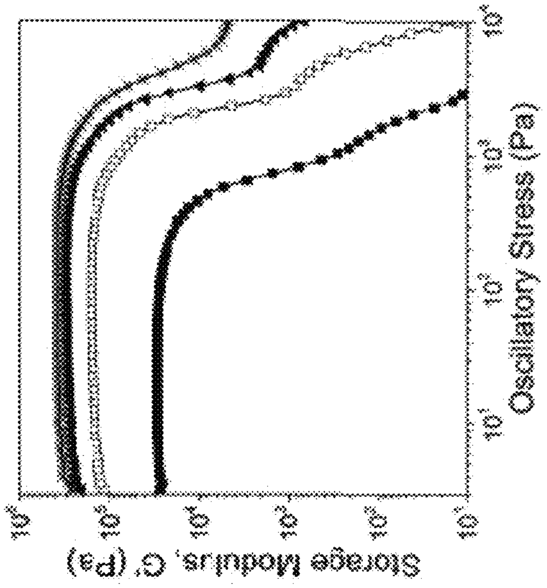
FIG. 3D is a plot of the effect of treated reinforcing silica filler on observed yield stress, according to various embodiments.

FIG. 3D is a plot of the effect of treated reinforcing silica filler (with a constant 1.0 wt. % rheological additive) on the observed yield stress of DIW inks. At a rheological additive concentration of 1.0 wt. %, loading of increasing concentrations of treated silica were studied to determine the appropriate quantity of silica necessary to print soft 3D materials. Oscillatory rheology was performed, demonstrating that at a relatively low loading of HMDZ-treated silica (10 wt. %, ■), the measured yield stress was 130 Pa, a value deemed too low for our 3D printing processes; yield stress values increased to 400 Pa, 545 Pa, and 690 Pa for silicone-based formulations comprising, 15 wt. % (□), 18 wt. % (▲), and 20 wt. % (*) HMDZ-treated silica, respectively. Thus, it was demonstrated that the rheology of the ink formulations may be tuned through an adjustment in silica loading.

Pt-Catalyzed Hydrosilylation Chemistry

A low color Karstedt Pt catalyst was selected as a platinum catalyst complex and 1-ethynyl-1-cyclohexanol (ETCH) was selected as the reaction inhibitor. To obtain inks with a long printable time windows, 300-400 ppm ETCH was added for 4-5 ppm Pt catalyst to sufficiently inhibit silicone curing while still providing rapid curing at elevated temperatures (ca. 125-150° C.).

Figure 4:
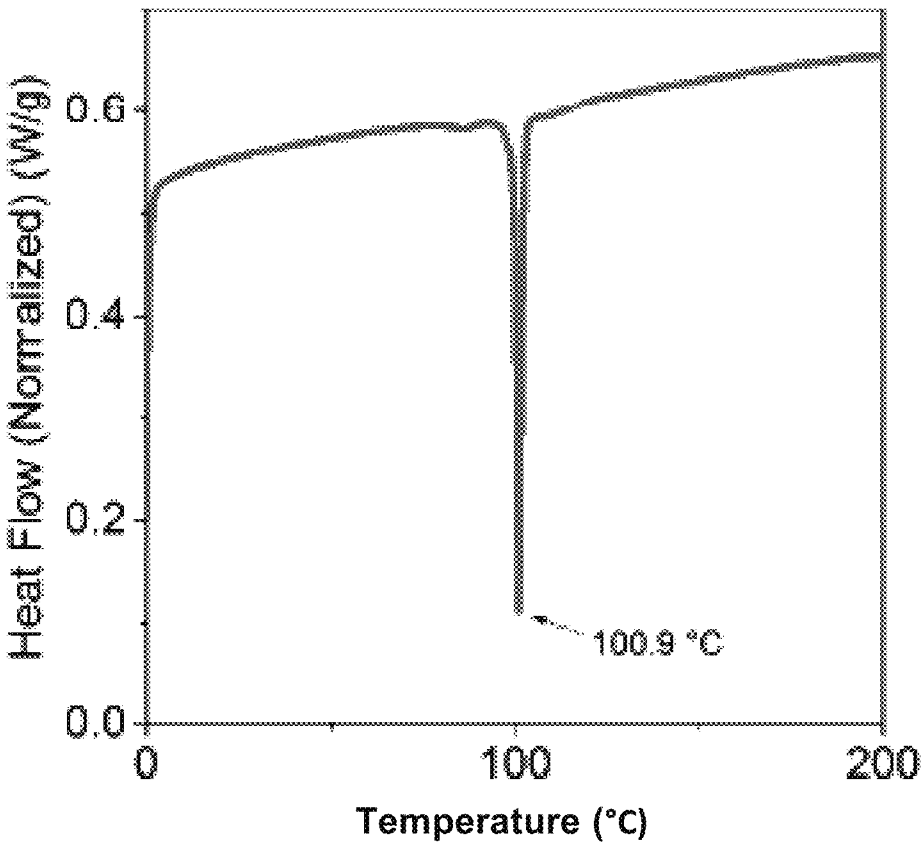
FIG. 4 is a plot of a normalized temperature sweep for a polysiloxane matrix, according to one embodiment.

FIG. 4 shows a normalized temperature sweep (x-axis) for a polysiloxane matrix containing 4 ppm Pt-Karstedt's catalyst and 500 ppm ETCH inhibitor in which the normalized heat flow of the polysiloxane matrix was measured (y-axis, W/g). As shown in FIG. 2, the onset of curing is indicated by the endothermic peak at 100.9° C.

Figure 5:
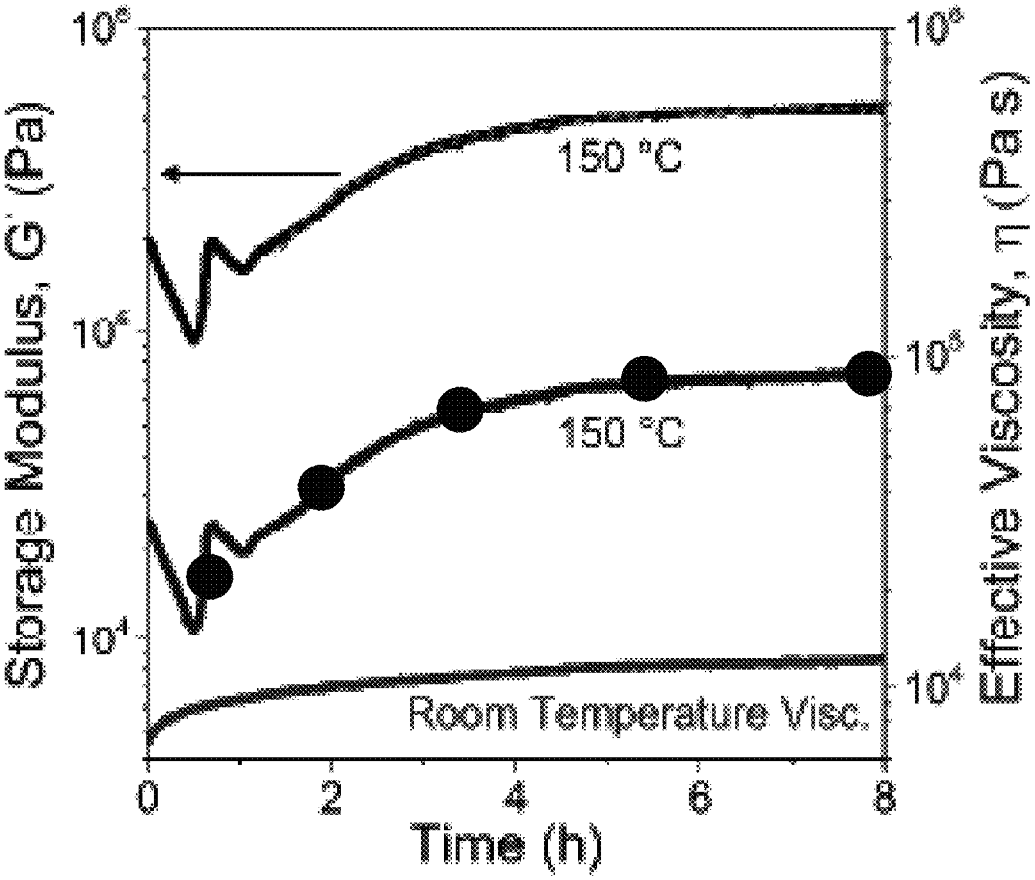
FIG. 5 is a plot of the oscillatory rheology of silicone-based inks at variable temperatures, according to one embodiment.

To analyze the working print time, a 3D printable silicone-based composite was prepared in the presence of 4 ppm Pt-Karstedt's catalyst, 400 ppm ETCH, and 1.0 equivalent of silane crosslinker. FIG. 5 shows the oscillatory rheology a 3D printable silicone-based composite at room temperature and at 150° C. over time, 0 to 8 hours (x-axis). From this analysis, the effective viscosity (right y-axis) of the silane-based composite remained stable with low viscosity and long pot life at room temperature for greater than 8 hours (bottom curve), whereas at 150° C., the effective viscosity curve (●) showed curing with a dramatic rise in viscosity could be initiated within the first hour of elevated temperature. Analysis of the storage modulus (left y-axis), showed a similar dramatic patterned curve at 150° C. (uppermost curve). Thus, this analysis showed printing with silicone-based inks as described may be stored over 24 hours after preparation; and storing inks in a cold environment may further prolong the pot life.

Figure 6B:
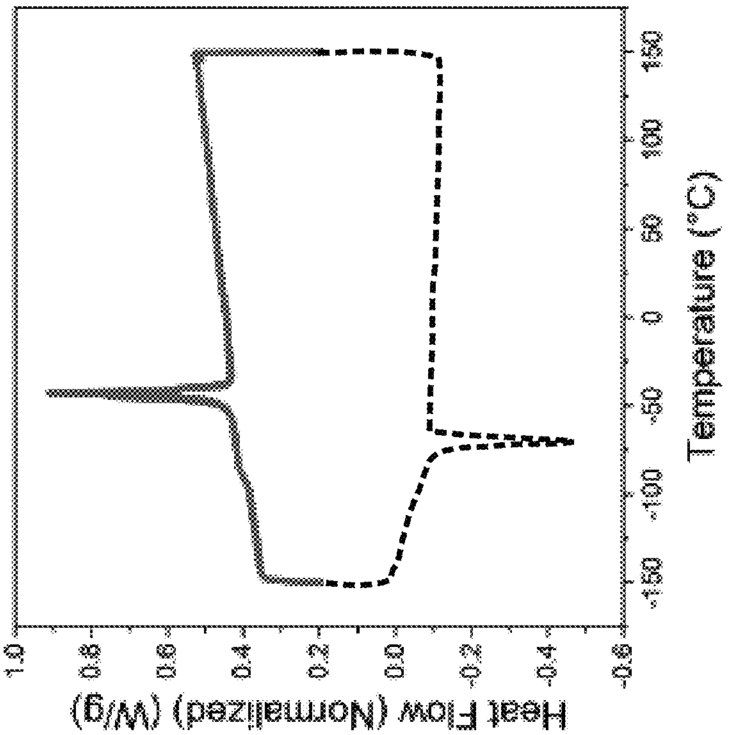
FIG. 6B is the DSC heating profile curves of standard PDMS material, according to one embodiment.
Figure 6A:
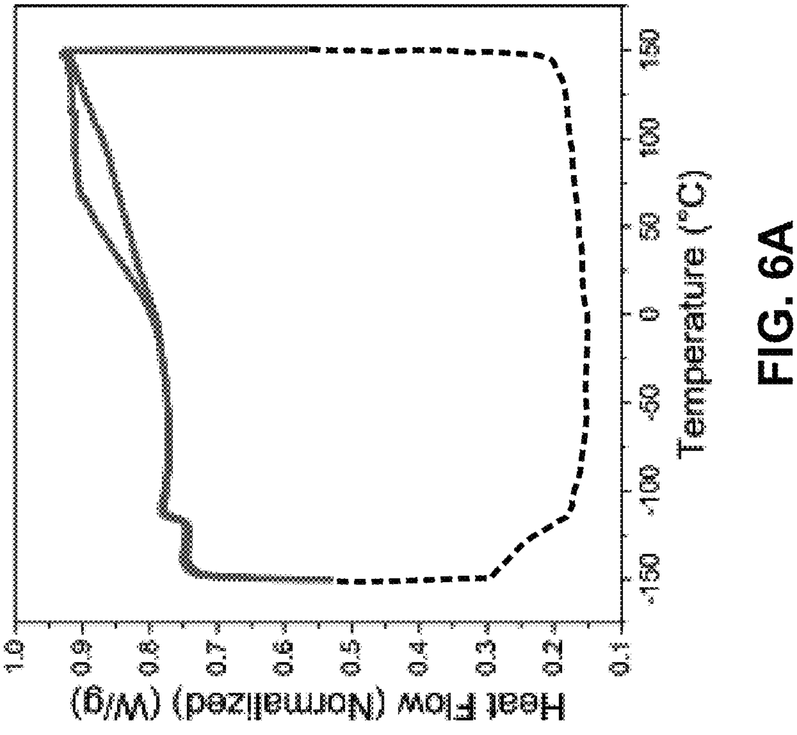
FIG. 6A is the DSC heating profile curves of silicone-based ink, according to one embodiment.

Silicone-Based Inks with Tunable Stiffness 3D printable silicone-based inks were prepared following Shore hardness durometer values 10A, 25A, 45A, 55A, 60A, and 70A, which were named MD-XXA, where XX corresponds to the Shore hardness. The complete formulation details for each material is shown on Table 1 (see above). FIGS. 6A and 6B show the DSC heating profiles for standard PDMS material (FIG. 6B) and polysiloxane ink MD-70A (FIG. 6A). The DSC heating profile involved a temperature ramp (solid curve) from −150° C. to 150° C. at a rate of 10° C. ° C./minute, followed by an isothermal hold for 1 minute and a cooling ramp (dashed curve) from 150 to −150° C. at a rate of 10° C./minute, followed by an isothermal hold for 1 min prior to a final temperature ramp (solid curve) from −150° C. to 150° C. at a rate of 10° C./minute.

FIG. 6B depicts the normalized DSC curve for a standard PDMS material, showing characteristic crystallization peak (dashed curve) and melting peak (solid curve). In contrast, FIG. 6A shows a normalized DSC curve for a characteristic variable stiffness polysiloxane ink (MD-70A) demonstrating the absence of crystallinity in the MD-70 material as a result of the use of the poly(dimethylsiloxane)-co-(diphenylsiloxane) macromer.

3D Printed Structures from Silicone-Based Ink

Figure 7B:
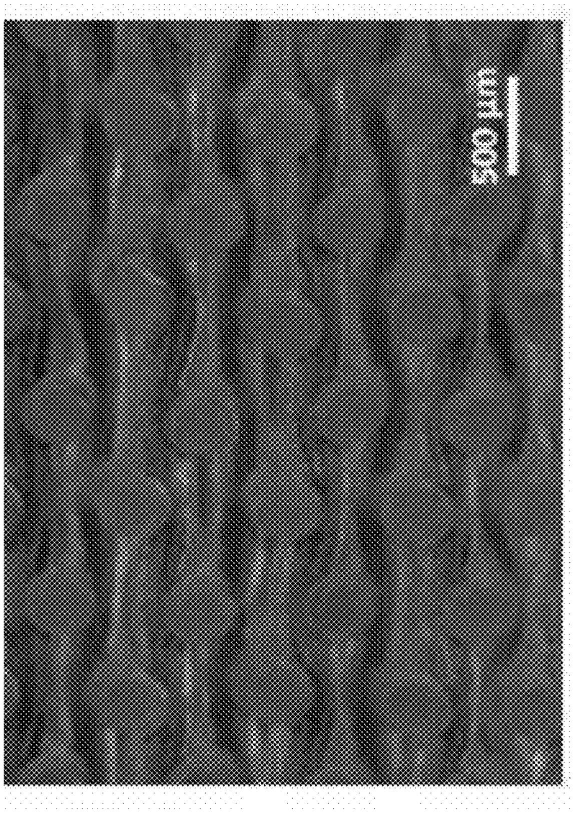
FIG. 7A-7B are cross-sectional images of lattice structures of silicone-based inks, according to various embodiments.
Figure 7A:
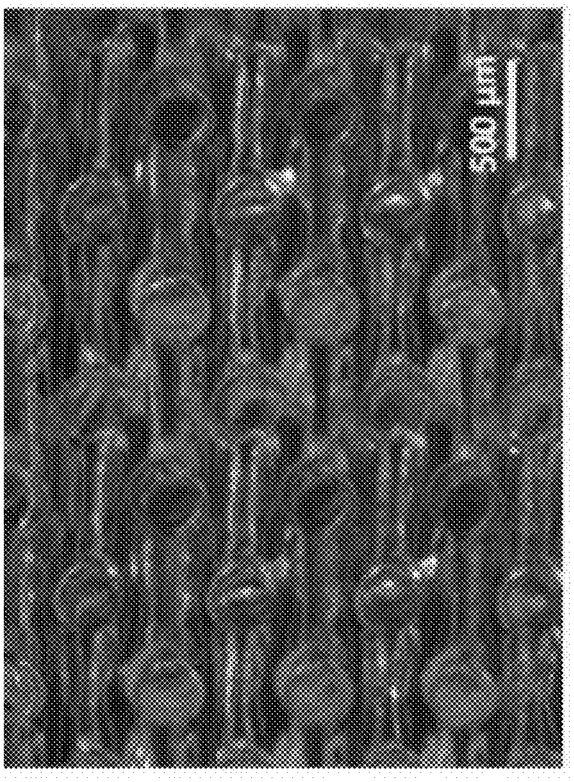

A representative cross-sectional image of lattice structures from 3D printing with silicone-based ink MD-10A is shown in FIG. 7A and with silicone-based ink MD-70A is shown in FIG. 7B. Each structure resulted in 28 printed layers with an FCT (face centered tetragonal) geometry, 1000 μm center-to-center spacing, and a 250 μm filament diameter.

Stiffness Tunability of Silicone-Based Ink for 3D Printing

Tensile and compression testing of silicone-based ink demonstrated stiffness tunability. FIGS. 8A-8D show the tensile and compression results for silicone-based inks MD-10A, MD-45A, and MD-70A. FIG. 8A shows a plot of tensile stress (y-axis) versus tensile strain (x-axis) of silicone-based inks MD-70D (■), MD-45A (●), and MD-10A (solid black line). The softest material, MD-10A, featured a Young's modulus of 0.40 MPa with an average elongation at break of 528%. MD-45A (●) featured a Young's modulus of 3.61 MPa with an average elongation at break 362%. The hardest material, MD-70A (■) featured a Young's modulus of 11.51 MPa with an average elongation at break of 77%.

The relative compressive performance of the silicone-based inks was measured by applying a cyclic compressive load of 2000 kPa to an 8 layer FCT lattice (500 μm center-to-center spacing, 250 μm filament diameter). FIG. 8B shows a summary of the compressive load deflection curves and peak compressive strain values of 59.2%, 56.6%, and 48.1% were measured after 3 successive load-unload cycles for MD-10A (solid line), MD-45A (●), and MD-70A (■), respectively. These results demonstrated hysteresis with regard to stable cyclic compressive loads.

A physical demonstration of the large difference in material properties at either end of the hardness spectrum is shown in FIGS. 8C and 8D. Observable variable stiffness of 3D printed silicone lattices evident through compression loading with 1200 g static weighted samples for MD-10A (FIG. 8C) and MD-70A (FIG. 8D);

FIG. 8E depicts the demonstration of the potential for soft robotic applications through the printing of a pneumatically-driven gripper comprised solely of MD-10A and MD-70A. An air-driven soft robotic actuator was 3D printed as a single component. Pressurization of the hollow interior channels comprising soft silicone (MD-10A) exhibiting high strength and low stiffness were able to expand and deflect the reinforcing frame of the actuator, which was printed with a stiff silicone material (MD-70A). Various forms of bio-inspired locomotion and bio-mimicry in the form of soft robotics applications could thus be engineered in a similar fashion.

Example Preparation of Single Emulsion, Dual Phase Separation Core-Shell Microspheres All chemicals were used without further purification. 14.45 mL of 2-part custom shell resin silicone or SRS, (50 durometer Shore A) or alternatively Dow Corning Sylgard 184 (Dow Corning, Midland, MI) is dispersed in 63.5 mL mineral oil (Sigma Aldrich, St. Louis, MO). Table 2 lists the components of Example 1 of a Shell-Resin-

TABLE 2

| Example 1 of Shell-Resin-Silicone | |
|---|---|
| Shell-Resin-Silicone (SRS) | Weight % (wt %) |
| Nusil PLY3-7560 | 70% |
| Milliken MQV-7 | 12% |
| Gelest HMS-H271 | 18% |
| Karstedt Pt catalyst | 25 ppm |
| 1-ethynyl-1-cyclohexanol (inhibitor) | 100 ppm |

Silicone mixtures. To this 35.4 mL of tetrahydrofuran (Sigma Aldrich) is added to create a miscible oil-PDMS phase. 100 mL of aqueous phase was prepared from premade stock solutions to the following concentrations: 8 wt % Poly(vinyl alcohol); (Mw 13-23 kDa, 87-89% hydrolyzed, Sigma Aldrich). Oil phase was then added to the aqueous phase all at once and emulsified with an IKA T25 Digital (IKA Works, Inc, Wilmington, NC) equipped with a S25-N19 stainless steel dispersing element set to 8500 rpm for 60 seconds. Emulsion was then heated on a hotplate equipped with a thermocouple to achieve an internal temperature of 70° C. for 16 hours to cure the silicone resin. After 2 hours at 70° C., a magnetic stir bar was added to the emulsion and gently stirred for the remaining cure period. After the elapsed cure period, the cured microsphere solution was allowed to cool to room temperature with constant stirring.

Example Preparation of Double Emulsion Core-Shell Microspheres 0.75 mL SIT 8173.0 (Gelest, Inc, Morrisville, PA) was dispersed in 19.0 mL low viscosity (800 cSt) MQ reinforced silicone resin. To this 50.8 mL perfluorodecalin (Sigma Aldrich) was slowly added with constant slow stirring to form the primary emulsion. 100 mL of aqueous phase was prepared from premade stock solutions to the following concentrations: 8 wt % Poly(vinyl alcohol); (Mw 13-23 kDa, 87-89% hydrolyzed, Sigma Aldrich), 2.5% Tween 60. The primary emulsion was then slowly added to the aqueous phase with emulsification utilizing an IKA T25 Digital equipped with a S25N-25F stainless steel dispersing element set to 6000 rpm for 90 seconds after completing addition. Emulsion was then heated on a hotplate equipped with a thermocouple and magnetic stir bar to achieve an internal temperature of 70° C. for 16 hours to cure the silicone resin. After the elapsed cure period, the cured microsphere solution was allowed to cool to room temperature with constant stirring.

Core-shell microspheres were isolated from aqueous solution via centrifuge (2000×g for 10 mins), taking care not to destroy the core-shell structure through excessive centrifugal force. Isolation by pouring off the supernatant and resuspension of the microballoons in milli-Q water was repeated a minimum of four times to remove residual surfactant from the microsphere surface. After the final rinse, microsphere paste was collected though vacuum filtration onto 40 Whatman paper, until a water content of ≤10 wt % was achieved. Water content of microsphere paste was analyzed by TGA, and general size distribution of microspheres were collected via microscope imaging (Carl Zeiss, Inc, Thornwood, NY) The microsphere fabrication procedure has been previously scaled up to yield up to 1.5 kg of usable microsphere paste. Core-shell microspheres were stored and used as a water-particle paste instead of drying to a powder to prevent caking and osmotic forces during dying that resulting in collapse of the microstructure.

Siloxane Ink Having Core-Shell Microspheres

Siloxane ink having core-shell microspheres was formulated to various porosities through differing loading of core-shell microspheres into the ink matrix. In a typical preparation of 40 core-vol % ink, 10 g of core-shell microsphere paste was mixed into 14.3 g of thixotropic silicone ink described herein using a Thinky planetary mixer (Thinky, Laguna Hills, CA) initially at 1500 rpm for 60 seconds to incorporate the microstructures into the matrix. This was followed by successive multiple mixings at 2000 rpm for 30 seconds, with a 30 second, 2200 rpm de-aeration period to drive residual water out of the formulated ink. Fully formulated ink was printed as previously described.

3D structures were printed using siloxane ink having core-shell microspheres as described. The image in FIG. 13A is a scanning electron micrograph image of a 3D structure printed with siloxane ink having core-shell microspheres. The liquid in the core of the core-shell microspheres was removed following formation of the structure. The image of FIG. 13B is a magnified view of a cross-section of a filament of the structure as shown in the image in FIG. 13A. As shown, the increased magnification of the filament of the structure depicts multiple pores formed by the core-shell microspheres in the material of the ligament. The images show intra-filament porosity.

FIGS. 13A and 13B show a 3D printed silicone-based part with pores formed from core-shell microspheres in the ink. FIG. 13B shows the magnified view of a cross-section of a filament with pores formed by the core-shell microspheres. In this approach, core-shell microspheres were extruded with the ink to form the continuous filaments of the 3D printed structure. The core-shell microspheres may have an average diameter of 1 to 20 μm, such that the release of the carrier liquid from the core-shell microspheres and the printed part post processing may result in intra-filament pores having an average diameter of 1 to 20 μm. In one approach, the shell (as indicated by an arrow on the image of part (b)) remains in the filament with only the core absent, leaving a void, pore, etc.

FIG. 13C shows an image slice of the 3D structure printed with siloxane ink having core-shell microspheres using micro computed tomography (CT) analysis. FIG. 13D is a 3D rendering of the structure from micro CT analysis.

Table 3 shows the physical characteristics of siloxane inks having core-shell microspheres (40p Ink, 60p Ink), as described herein. 40p Ink is formulated at 40 vol % encapsulated microsphere core fluid/oil within the ink, similarly, 60p Ink is 60 vol % encapsulated microsphere core fluid/oil within the ink. The characteristics listed in Table 3 include yield stress or point of shear thinning of the uncured ink, average compression set % (per ASTM D395, Method B) of the printed part formed with the respective ink, and average density of the printed and post-processed part indicating relative void volume. The density of non-microsphere ink is approximately 1.05 g/cc. 60p Ink has a reduced density due to structural collapse.

TABLE 3

Physical characteristics of siloxane inks having core-shell microspheres and the products formed with the ink

| Ink | Yield Stress (Pa) | Printed Part Average Compression Set % | Average Density (g/cc) |
|---|---|---|---|
| 40p Ink | 879.5, 1152.4 | 4.02 | 0.448 |
| 60p Ink | 2023.2, 2347.3 | 4.99 | 0.507 |

Figure 14A:
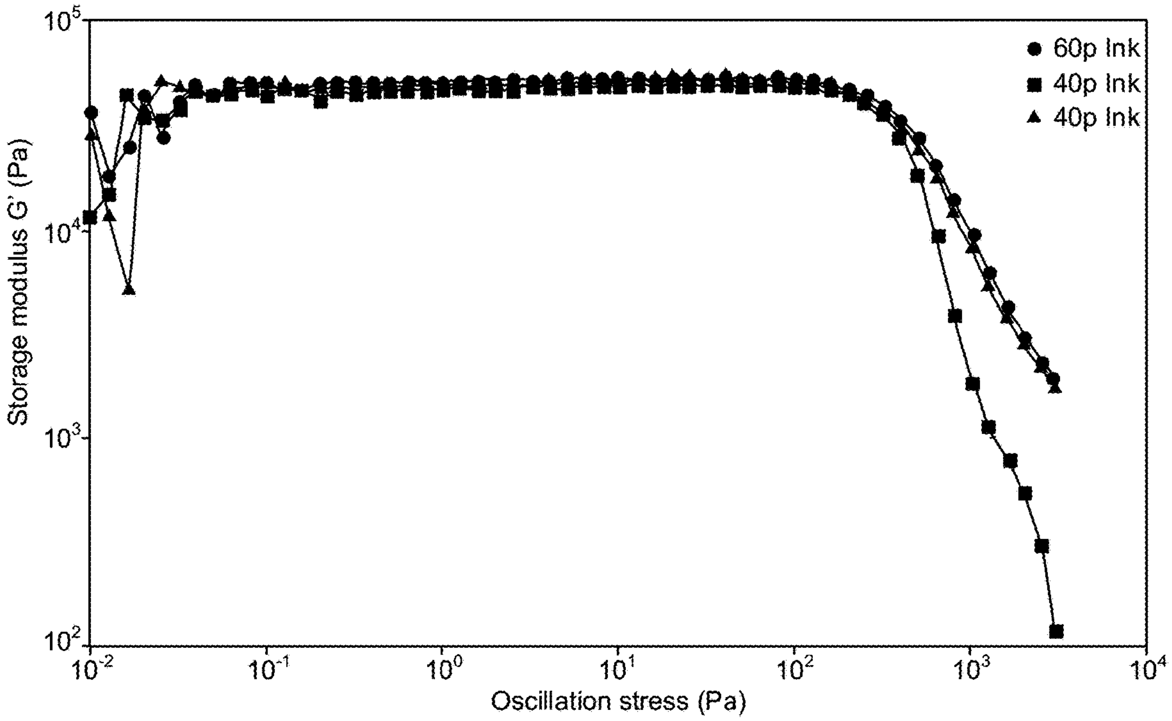
FIG. 14A is a plot of storage modulus of three different inks, according to various embodiments.
Figure 14B:
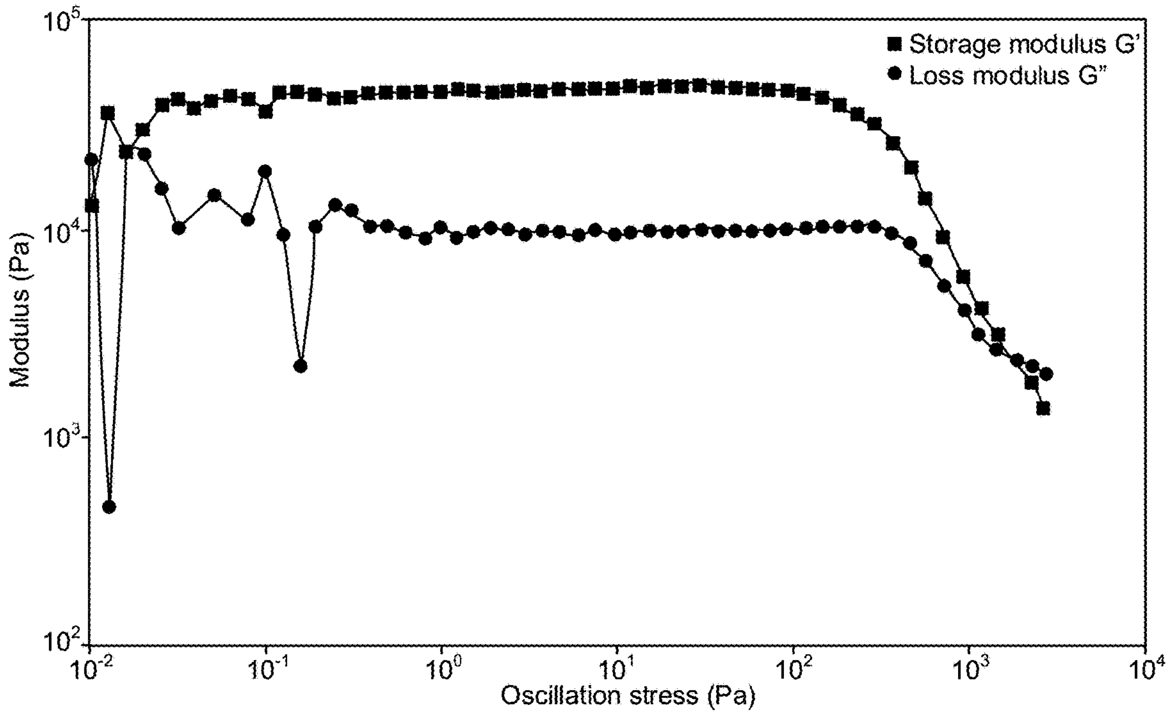
FIG. 14B is a plot of storage modulus versus loss modulus of an ink, according to one embodiment.

FIGS. 14A and 14B represent plots of rheology of various siloxane inks having core-shell microspheres, as described herein. FIG. 14A is a plot of Storage Modulus of three inks in terms of oscillation stress. The pattern of storage modulus for all three inks was similar, and one of the 40p Inks (■) demonstrating a sharper decline in storage modulus with increased oscillation stress. FIG. 14B is a plot comparing storage modulus (■) to loss modulus (●) of the 60p Ink, the 60 vol % encapsulated microsphere core fluid/oil within the siloxane ink.

In Use

Functional 3D printed soft materials have a diverse range of applications and potential within the fields of materials engineering, bioengineering, and electronics. Through precise control over the deposition of highly-engineered viscoelastic inks in the form of continuous filaments, complex 3D architectures may be additively fabricated, layer-by-layer, to generate parts that are directly applicable to cutting-edge technologies, including aerospace and defense, microwave optics, supercapacitors, piezoelectrics, and mechanical metamaterials. In particular, 3D printed silicones may be well suited to soft materials applications including high-performance foams and cellular-solids, soft robots, and flexible and stretchable electronics. Various embodiments may be used to 3D print biomedical devices and biological scaffolds that exhibit controlled and targeted drug release, prosthetics, hierarchically porous foams, sensors, self-healing materials, and metamaterials.

Various embodiments described herein may be applied to 3D engineered cellular solids, foam structures, shock-absorbing cushions, soft robotics, biomedical devices with intrinsic biocompatibility, prosthetics, metamaterials, flexible electronics, and optic systems. Additionally, the low temperature performance, down to negative 150° C., may be suitable to applications in extreme conditions such as space or cryogenic pharmaceutical storage.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A silicone-based ink for additive manufacturing, the ink comprising:
- a vinyl-terminated diphenyl siloxane macromer;
- a treated silica hydrophobic reinforcing filler;
- a rheology modifying additive; and
- a plurality of core-shell microspheres, wherein each core-shell microsphere comprises:
  - a polyorganosiloxane shell, and
  - at least one core inside the shell, the at least one core having a carrier and at least one component, wherein the at least one component is configured to be released post processing,
- wherein an average diameter of the cores of the plurality of core-shell microspheres is in a range of greater than 2 microns to less than about 100 microns.

2. The ink as recited in claim 1, wherein an average diameter of core-shell microspheres is in a range of greater than about 1 micron to less than about 100 microns.

3. The ink as recited in claim 1, wherein an average diameter of core-shell microspheres is in a range of greater than about 10 micron to less than about 30 microns.

4. The ink as recited in claim 1, wherein the polyorganosiloxane shell comprises polydimethylsiloxane diphenylsiloxane and a reinforcing filler.

5. The ink as recited in claim 4, wherein the reinforcing filler is trimethylsiloxysilicate graft polydimethylsiloxane.

6. The ink as recited in claim 1, wherein the at least one component comprises at least one material selected from the group consisting of: a compound for pharmaceutical application, a monomer, an oligomer, a polymer, a catalyst, and a combination thereof.

7. The ink as recited in claim 1, wherein the core-shell microspheres comprise a first core-shell microsphere and a second core-shell microsphere, wherein the at least one component of the first core-shell microsphere is different from the at least one component of the second core-shell microsphere.

8. The ink as recited in claim 7, wherein the at least one component of the first core-shell microsphere is configured to be released from the first core-shell microsphere at a first time, wherein the at least one component of the second core-shell microsphere is configured to be released from the second core-shell microsphere at a second time, wherein the first time is different from the second time.

9. The ink as recited in claim 1, wherein the ink is stable without crystallinity at a temperature in a range of −45° C. to −150° C.

10. The ink as recited in claim 1, wherein the average diameter of the cores is in a range of greater than about 10 microns to less than about 30 microns.

11. The ink as recited in claim 1, wherein the polyorganosiloxane shell comprises polydimethylsiloxane diphenylsiloxane and a reinforcing filler.

12. The ink as recited in claim 11, wherein the reinforcing filler is selected from the group consisting of: trimethylsiloxysilicate graft polydimethylsiloxane and fumed silica.

13. The ink as recited in claim 11, wherein the at least one component comprises at least one material selected from the group consisting of: a compound for pharmaceutical application, a monomer, an oligomer, a polymer, a catalyst, and a combination thereof.

14. The ink as recited in claim 11, wherein the carrier includes an oil, wherein the oil is at least partially immiscible with a siloxane resin.

15. The ink as recited in claim 1, wherein the carrier includes a liquid having a boiling point in a range of about 50° C. to about 200° C.

16. The ink as recited in claim 1, wherein the plurality of core-shell microspheres includes a porogen.

17. The ink as recited in claim 15, wherein the liquid includes perfluorocarbon.

18. A product of additive manufacturing having a plurality of continuous filaments formed of the ink of claim 1, the product comprising:

the vinyl-terminated diphenyl siloxane macromer,
the hydrophobic reinforcing filler,
the rheology modifying additive, and
the plurality of core-shell microspheres.

19. The product as recited in claim 18, wherein the product is a silicone-based three-dimensional structure, wherein an average diameter of the filaments of the three-dimensional structure is greater than about 100 microns, wherein a ratio of an average diameter of core-shell microspheres to the average diameter of the filaments is in a range of greater than 1:100 to less than 3:4.

20. The product as recited in claim 18, wherein an average diameter of core-shell microspheres is in a range of greater than about 10 micron to less than about 30 microns.

21. The product as recited in claim 18, wherein the core-shell microspheres comprise the polyorganosiloxane shell and the core inside the shell, the core having the carrier and at least one component, wherein the at least one component is configured to be released post processing.

22. The product as recited in claim 21, wherein the at least one component comprises at least one material selected from the group consisting of: a compound for pharmaceutical application, a monomer, an oligomer, a polymer, a catalyst, and a combination thereof.

23. The product as recited in claim 21, wherein the at least one component is configured to be released from the product.

24. The product as recited in claim 21, wherein the product comprises a first core-shell microsphere and a second core-shell microsphere, wherein the at least one component of the first core-shell microsphere is different from the at least one component of the second core-shell microsphere.

25. The product as recited in claim 24, wherein the at least one component of the first core-shell microsphere is configured to be released from the product at a first time, wherein the at least one component of the second core-shell microsphere is configured to be released from the product at a second time, wherein the first time is different from the second time.

26. The product as recited in claim 18, wherein the core-shell microspheres comprise the polyorganosiloxane shell and the core inside the shell, the core having the carrier, wherein the carrier is configured to be released from the core-shell microspheres, wherein the carrier is released post processing of the product, wherein the core-shell microspheres without carrier are pores in the product.

27. The ink as recited in claim 1, wherein the carrier includes an oil, wherein the oil is at least partially immiscible with a siloxane resin.

28. The ink as recited in claim 1, wherein the carrier includes a liquid having a boiling point in a range of about 50° C. to about 200° C.

29. The ink as recited in claim 1, wherein the core-shell microspheres are a porogen.

30. The ink as recited in claim 1, wherein each core-shell microsphere has at least one core inside the shell.

31. The ink as recited in claim 1, wherein at least some of the core-shell microspheres have greater than one core inside the shell.

* * * * *